(12) United States Patent
Ballas et al.

(10) Patent No.: US 9,885,059 B2
(45) Date of Patent: Feb. 6, 2018

(54) ULTRAHIGH THROUGHPUT MICROINJECTION DEVICE

(71) Applicants: Indiana University Research and Technology Corporation, Indianapolis, IN (US); The Regents of the University of California, Oakland, CA (US)

(72) Inventors: Chris Ballas, Fishers, IN (US); Masa Rao, Riverside, CA (US); Yanyan Zhang, Houston, TX (US)

(73) Assignees: Indiana University Research and Technology Corporation, Indianapolis, IN (US); The Regents of the University of California, Oakland, CA (US)

( * ) Notice: Subject to any disclaimer, the term of this patent is extended or adjusted under 35 U.S.C. 154(b) by 237 days.

(21) Appl. No.: 14/379,486

(22) PCT Filed: Feb. 21, 2013

(86) PCT No.: PCT/US2013/027116
§ 371 (c)(1),
(2) Date: Aug. 18, 2014

(87) PCT Pub. No.: WO2013/126556
PCT Pub. Date: Aug. 29, 2013

(65) Prior Publication Data
US 2015/0299729 A1    Oct. 22, 2015

Related U.S. Application Data

(60) Provisional application No. 61/601,383, filed on Feb. 21, 2012.

(51) Int. Cl.
*C12M 1/00* (2006.01)
*C12M 3/00* (2006.01)
(Continued)

(52) U.S. Cl.
CPC .......... *C12N 15/89* (2013.01); *B01J 19/0046* (2013.01); *C12M 23/12* (2013.01);
(Continued)

(58) Field of Classification Search
CPC . C12M 35/00; C12M 35/02; B01L 3/502761; B01L 3/50273
See application file for complete search history.

(56) References Cited

U.S. PATENT DOCUMENTS 5,262,128 A * 11/1993 Leighton ............... B01L 3/0244
422/522
6,846,668 B1 * 1/2005 Garman .................. C12M 35/00
435/285.1

(Continued)

OTHER PUBLICATIONS

Chen et al., "Micro injection molding of a micro-fluidic platform," International Communications in Heat and Mass Transfer, 37(9):1290-1294, Aug. 5, 2010.

(Continued)

*Primary Examiner* — Nathan Bowers
(74) *Attorney, Agent, or Firm* — Knobbe, Martens, Olson & Bear, LLP

(57) ABSTRACT

Many applications in cell biology, genetic engineering, cell-based therapeutics, and drug discovery require precise and safe methods for introducing membrane-impermeable molecules into cells. This can be implemented satisfactorily by microinjection. However, disadvantages of traditional manual microinjection include high degree of operator skill, low throughput and labor-intensiveness. Many studies have focused on developing automated and high-throughput systems for microinjection to address these limitations. However, none have provided sufficient throughput for applications such as ex vivo cell therapy, where manipulation of many cells is helpful.

24 Claims, 31 Drawing Sheets

(51) Int. Cl.
  *B01L 3/00* (2006.01)
  *C12N 15/89* (2006.01)
  *C12M 1/32* (2006.01)
  *B01J 19/00* (2006.01)

(52) U.S. Cl.
  CPC .............. *B01J 2219/00452* (2013.01); *B01J 2219/00502* (2013.01); *B01J 2219/00587* (2013.01); *B01J 2219/00743* (2013.01)

(56) References Cited

U.S. PATENT DOCUMENTS

| | | | | |
|---|---|---|---|---|
| 6,998,265 | B2* | 2/2006 | Banes | C12M 25/14 435/305.1 |
| 7,390,648 | B1* | 6/2008 | Palacios-Boyce | C12M 21/06 422/64 |
| 7,807,107 | B2 | 10/2010 | Tamai et al. | |
| 2004/0000901 | A1* | 1/2004 | Sui | G01N 33/48728 324/200 |
| 2004/0063100 | A1* | 4/2004 | Wang | B81B 1/008 435/6.11 |
| 2006/0128006 | A1 | 6/2006 | Gerhardt et al. | |
| 2007/0264705 | A1* | 11/2007 | Dodgson | A61B 17/435 435/283.1 |

OTHER PUBLICATIONS

Chung et al., "Highly-efficient single-cell capture in microfluidic array chips using differential hydrodynamic guiding structures," Applied Physics Letters, 98(12):123701.1-123701.3, Mar. 21, 2011.
Heo, Joo Hyung, International Search Report, PCT/US2013/027116, Korean Intellectual Property Office, dated Jun. 3, 2013.
Zhang et al., "Design and fabrication of MEMS-based microneedle arrays for medical applications," Microsystem Technologies, 15(7):1073-1082, May 20, 2009.
Bacamel, Philippe, International Preliminary Report on Patentability, International Application No. PCT/US2013/027116, dated Sep. 4, 2014.

* cited by examiner

A  a) Cell aliquoting b) Cell capture, permeabilization, & wash c) Cell release & collection

C

D

C

D

B

C

A

B

C

D

ULTRAHIGH THROUGHPUT MICROINJECTION DEVICE

CROSS REFERENCE TO RELATED APPLICATION

This application is a U.S. National Stage Application filed under 35 U.S.C. § 371 and claims priority to Application No. PCT/US2013/027116, filed Feb. 21, 2013, which application claims the benefit of priority to U.S. Provisional Patent Application Ser. No. 61/601,383, filed Feb. 21, 2012, the disclosure of which are incorporated herein by reference.

GOVERNMENT RIGHTS

This invention was made with government support under RR026253 awarded by National Institutes of Health. The U.S. Government has certain rights in the invention.

FIELD OF THE INVENTION

Various embodiments of the inventions described herein pertain to the manipulation of biological cells, and in some embodiments to the introduction of a material into the cells.

BACKGROUND OF THE INVENTION

Microinjection is a well-established cellular manipulation technique that enables introduction of exogenous materials into a cell through insertion of an extremely fine hollow needle. When working with non-adherent cells, conventional microinjection instrumentation typically requires an operator to locate the cell to be manipulated using an optical microscope and then capture it using aspiration (i.e. suction) from a blunt-tipped micropipette attached to a manually controlled micromanipulator. Using a separate manually-controlled micromanipulator, the operator then guides the needle towards the captured cell and inserts it for injection. Once completed, the operator retracts the needle and releases the cell by reversing the direction of aspiration flow. This procedure is then repeated in a serialized manner until sufficient numbers of cells have been manipulated for the intended application.

While microinjection is widely used in the engineering of cell lines, oocytes, and embryonic stem cells for transgenic animal generation and in vitro fertilization, its reliance upon skilled labor nonetheless limits its availability, since new operators require many months of training to develop proficiency. Moreover, the combination of manual operation and serialized injection methodology limits throughput (~3 cells/min and 100-1,000 cells/day, depending on the cell type and operator skill), which constrains progress in many current applications, and precludes use in others where microinjection may otherwise hold great promise.

SUMMARY OF THE INVENTION

One aspect of the present invention pertains to an apparatus for manipulation of biological cells. One embodiment includes a substrate having surface and a plurality of depressions or wells, each adapted and configured to capture a single cell, the surface of each well including a port in fluid communication with a port of each said other well, each said well including a projection extending toward the surface of the substrate.

Another aspect of the present invention pertains to an apparatus for manipulation of biological cells. One embodiment includes a first source of fluid at a first pressure, a second source of fluid at a second pressure, and a substrate having surface and a plurality of capture sites, each site being adapted and configured to hold therein at least a portion of one of the cells. Each site includes a first port in fluid communication with said first source, and a second port in fluid communication with said second source.

In some embodiments the second port is in fluid communication with a lumen within a localized projection within a capture site, and material can be introduced into a cell that has been ruptured on the projection by means of the lumen and port. Further, in some embodiments the device includes capture sites having projections that are in fluid communication by way of a lumen and port with a first material and first fluid, and yet other capture sites having lumens in fluid communication with a different material and different source of fluid, such that cells captured on one array can have different materials injected into their interiors.

Yet another aspect of the present invention pertains to a method for manipulating a biological cell, including a substrate having a surface and a depression in that surface. Still other embodiments include capturing a plurality of cells within each depression; and applying a pressure differential on the captured cells. One method includes simultaneously rupturing the walls of each of the cells.

Some aspects of the present invention pertain to the capture, puncture, and washing away of excess cells before puncturing the captured cells. However, the present invention is not limited to that order of processing. Yet other embodiments, as an example, pertain to the capture of cells, washing away of excess cells, the puncturing of the captured cells after washing away the excess, and the subsequent release of the punctured cells.

Still further, yet other aspects of the present invention pertain to the passive diffusion of material into cells, and yet other embodiments pertain to the active injection of material into the cells. For example, for the case of permeabilized cells, material that it is desired to diffuse into the cell is exposed to the ruptured cell before the rupture is closed by the cell. Yet other embodiments include the aspect of actively injecting material through the puncture site, such as with a penetrator having a lumen, the lumen being in fluid communication with the material to be injected. It is further noted that any kind of material or combinations of materials can be delivered to the cells either passively or actively. In some embodiments one of the materials delivered to the cells can include a dye that allows the cell to be separated from the cells that have not been penetrated or injected, and the nonpunctured-noninjected cells may be returned to the pool of prospective cells.

Still further embodiments pertain to the integration of the various devices and methods described herein with various sensing modalities, including the integration of lab-on-chip type functionality with various devices disclosed herein. Examples of such modalities and functionalities include analysis systems such as PCR, Luminex, flow cytometry, high content screening, and others.

It will be appreciated that the various apparatus and methods described in this summary section, as well as elsewhere in this application, can be expressed as a large number of different combinations and subcombinations. All such useful, novel, and inventive combinations and subcombinations are contemplated herein, it being recognized that the explicit expression of each of these combinations is unnecessary.

BRIEF DESCRIPTION OF THE DRAWINGS

Some of the figures shown herein may include dimensions. Further, some of the figures shown herein may have been created from scaled drawings or from photographs that are scalable. It is understood that such dimensions, or the relative scaling within a figure, are by way of example, and not to be construed as limiting.

FIG. 23 a) is a schematic representation of a portion of a UHT active microinjection device according to another embodiment. b is a schematic representation of a portion of a UHT active microinjection device as taken along line A-A of a.

DESCRIPTION OF THE PREFERRED EMBODIMENT

Figure 1:
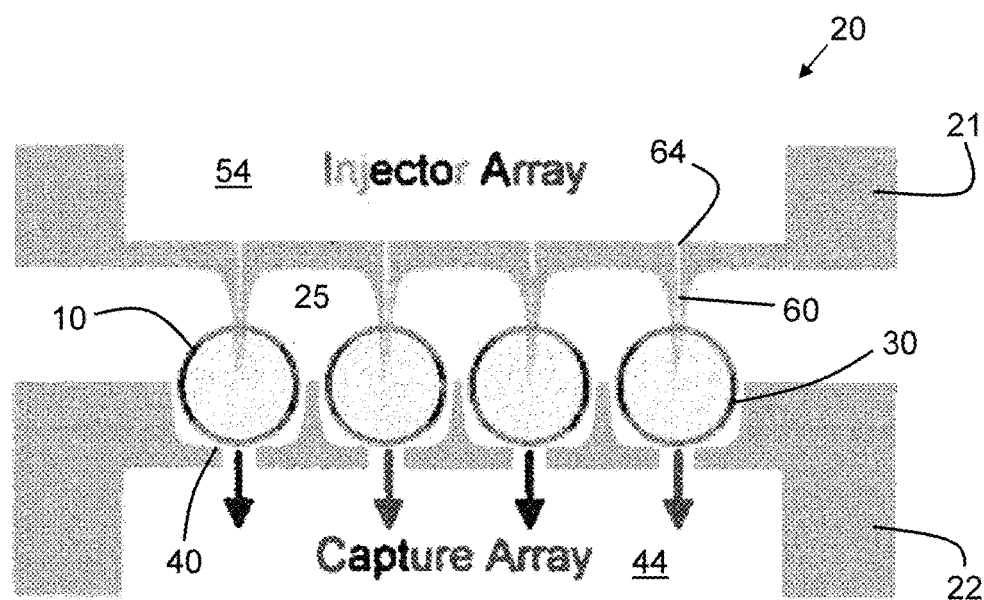
FIG. 1 is a schematic representation of an existing dual chip microelectromechanical systems (MEMS) concept for ultrahigh throughput (UHT) microinjection. Cells are injected when the Injector Array chip is moved towards the Capture Array chip. Arrows indicate direction of fluid flow used for aspiration-based cell capture.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates. At least one embodiment of the present invention will be described and shown, and this application may show and/or describe other embodiments of the present invention. It is understood that any reference to "the invention" is a reference to an embodiment of a family of inventions, with no single embodiment including an apparatus, process, or composition that should be included in all embodiments, unless otherwise stated. Further, although there may be discussion with regards to "advantages" provided by some embodiments of the present invention, it is understood that yet other embodiments may not include those same advantages, or may include yet different advantages. Any advantages described herein are not to be construed as limiting to any of the claims. The usage of words indicating preference, such as "preferably," refers to features and aspects that are present in at least one embodiment, but which are optional for some embodiments.

The use of an N-series prefix for an element number (NXX.XX) refers to an element that is the same as the non-prefixed element (XX.XX), except as shown and described. As an example, an element 1020.1 would be the same as element 20.1, except for those different features of element 1020.1 shown and described. Further, common elements and common features of related elements may be drawn in the same manner in different figures, and/or use the same symbology in different figures. As such, it is not necessary to describe the features of 1020.1 and 20.1 that are the same, since these common features are apparent to a person of ordinary skill in the related field of technology. Further, it is understood that the features 1020.1 and 20.1 may be backward compatible, such that a feature (NXX.XX) may include features compatible with other variant and embodiments (MXX.XX), as would be understood by those of ordinary skill in the art. This description convention also applies to the use of prime ('), double prime ("), and triple prime (''') suffixed element numbers. Therefore, it is not necessary to describe the features of 20.1, 20.1', 20.1", and 20.1''' that are the same, since these common features are apparent to persons of ordinary skill in the related field of technology.

Although various specific quantities (spatial dimensions, temperatures, pressures, times, force, resistance, current, voltage, concentrations, wavelengths, frequencies, heat transfer coefficients, dimensionless parameters, etc.) may be stated herein, such specific quantities are presented as examples only, and further, unless otherwise noted, are approximate values, and should be considered as if the word "about" prefaced each quantity. Further, with discussion pertaining to a specific composition of matter, that description is by example only, and does not limit the applicability of other species of that composition, nor does it limit the applicability of other compositions unrelated to the cited composition.

What will be shown and described herein, along with various embodiments of the present invention, is discussion of one or more tests that were performed. It is understood that such examples are by way of example only, and are not to be construed as being limitations on any embodiment of the present invention. It is understood that embodiments of the present invention are not necessarily limited to or described by the mathematical analysis presented herein.

Microinjection is a cellular manipulation technique that enables introduction of exogenous materials into cells through insertion of a fine hollow needle. It represents the "gold standard" for cellular manipulation, due to its precision, safety, and applicability to a wide variety of cell types and molecules. As such, it has served as a fundamental enabler for a broad range of biomedical and clinical applications. However, the reliance of current microinjection instrumentation on skilled human operators and serialized injection methodologies limits availability and throughput (~3 cells/min), thus hampering progress in many areas, e.g. RNA interference studies. These limitations have also constrained use in other applications, e.g. ex vivo cell therapies, where microinjection may address critical limitations of current bulk manipulation techniques, e.g. non-quantitative delivery, viral vector safety. Recent automation efforts have shown promise for improving success rates, but at the expense of instrument complexity. Moreover, only modest gains in throughput have been achieved (≤35 cells/min) and further improvement is limited by continuing reliance upon serialized injection methodologies. Herein, is described development of MEMS-based instrumentation that not only automates the microinjection process, but also radically enhances throughput via massive parallelization.

One embodiment of the present invention automates and massively parallelizes the microinjection process, thus providing potential for minimized demand upon the operator and UHT on the order of many thousands of cells/min. MEMS provide potential for unprecedented sensitivity, precision, and control in many biomedical applications, thus stimulating intense R&D effort in this area. However, surprisingly little effort has focused on the use of MEMS in microinjection, and the few efforts reported to date have failed to fully realize the potential embodied in MEMS. For example, some have created microfabricated injectors to improve reproducibility of injection, while others have used microfabricated substrates for capture of cells in ordered arrays to facilitate cell identification and alignment. However, utility for UHT microinjection is limited by continuing reliance on serialized injection methodologies.

One aspect of MEMS lies in the opportunity it provides for massive parallelization through creation of large arrays of microscale structures in a reproducible and cost-effective manner. An existing approach for exploiting such capability, shown in FIG. 1, uses a dual chip architecture in which a Capture Array chip positions cells for injection by a complimentary Injector Array chip. While potential for scalability is evident, limitation arises from the need for precise chip-to-chip alignment (translation, rotation, and parallelism), which adds complexity, particularly as cell size decreases and array size increases.

Figure 2:
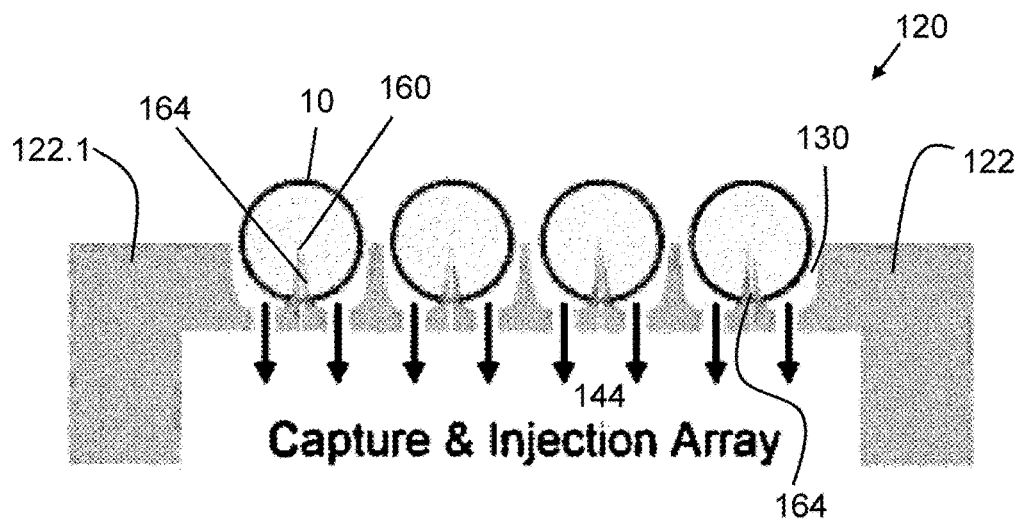
FIG. 2 is a schematic representation of a single chip MEMS concept for UHT microinjection according to one embodiment of the present invention. Arrows denote direction of fluid flow for aspiration-based capture. Cells are penetrated upon capture.

One embodiment of the present invention pertains to a MEMS approach, illustrated in FIG. 2, where functions are monolithically integrated within a single chip. In this approach, the Injectors are integrated directly within the Capture Sites, thus enabling penetration upon capture. This minimizes the need for a secondary chip and associated alignment, thus simplifying instrumentation relative to the dual chip MEMS approach. This also minimizes the need for machine vision identification of cells and precise control of injector movement, thus offering simplification relative to robotic instrumentation. Finally, since injector length and position are fixed, likelihood of over-insertion is minimized, and risk of Injector damage due to accidental contact with other device structures is minimized. This, therefore, provides potential for enhanced reproducibility and reliability relative to other approaches.

In one embodiment there is an out-of-plane configuration of the UHT microinjection device architecture which inherently lends itself to fabrication of extremely high density arrays, and which allows manipulation of large numbers of cells in a single capture cycle (e.g. $10^4$ cells but scalable to far greater numbers of cells if needed). Moreover, when coupled with a computer-controlled microfluidic cell handling subsystem that enables numerous capture cycles to be performed in succession, there can be throughputs that are many orders of magnitude greater than the current state-of-the-art (e.g. $\geq 10^4$ cells/min in some embodiments vs. $\leq 35$ cells/min for exiting devices). Moreover, the inherent simplicity allows implementation in a low-cost format that requires minimal operator skill or involvement.

An apparatus 120 according to one embodiment of the present invention is schematically depicted in FIG. 2. Apparatus 120 includes a substrate 122 that includes a plurality of depressions or wells 130, each of which is adapted and configured to hold a biological cell 10. Although the cell is shown contained within well 130, it is understood that well 130 may have a boundary that is smaller than the diameter than the cell, such that the cell rests on top of the well, and only portions of the cell enter the well.

Each well 130 includes a port 140 in the bottom of the well that provides fluid communication from the interior of well 30 to a source 44 of fluid. As cells 10 flow within the channel 25 between array 21 and substrate 22, the cells are attracted to wells 30 by maintaining source 44 at a pressure that is lower than the pressure in flow channel 25.

FIG. 2 shows projections 160 that are incorporated into corresponding wells 130 of substrate 122. Preferably, each projection is generally centered within well 130, although various embodiments contemplate projections located anywhere within well 130, including projections extending from the side walls. Further, although relatively sharp projections are shown herein (both schematically and photographically), it is understood that the projection can be of any shape sufficient to rupture the wall of the cell when the contact stress of the projection acting against the cell wall is sufficiently high. In some embodiments, the projections 130 include a lumen 164 through which material 12 within a fluid from source 154 can be provided to ruptured cells, although various embodiments of the present invention further contemplate solid projections without lumens. Preferably, projections 160 are integrated into substrate 122, and therefore do not move relative to wells 130. However, the present invention also contemplates those embodiments in which the plurality of projections are part of an injector array 121 that is movable relative to substrate 122, but located beneath the top surface 122.1 of substrate 122.

As cells 10 are presented in a reservoir or flow channel 125 to the wells 130, hydrodynamic drag on the cells 10 produced by negative fluid flow through the aspiration vias 140 (i.e., in the direction pictured) results in wells 130 capturing individual cells 10. Preferably, the flow rate through the aspiration vias 140 should be sufficient to locate each cell 10 within a corresponding well 130, but not sufficient to cause the cell wall to be penetrated by the projection 160. However, once cells 10 are located in wells 130, a subsequent increase in flow rate through the aspiration via 140 results in increased contact stress between tip 166 of each projection 160 and the wall of the cell 10 which results in a local rupturing 14 of the cell wall. Assembly 120 further includes a lumen 164 within each projection 160. These lumens are provided with fluid from a source that is not pictured in FIG. 2 (for the sake of clarity) as will be explained further with regards to FIG. 13b.

Figure 3:
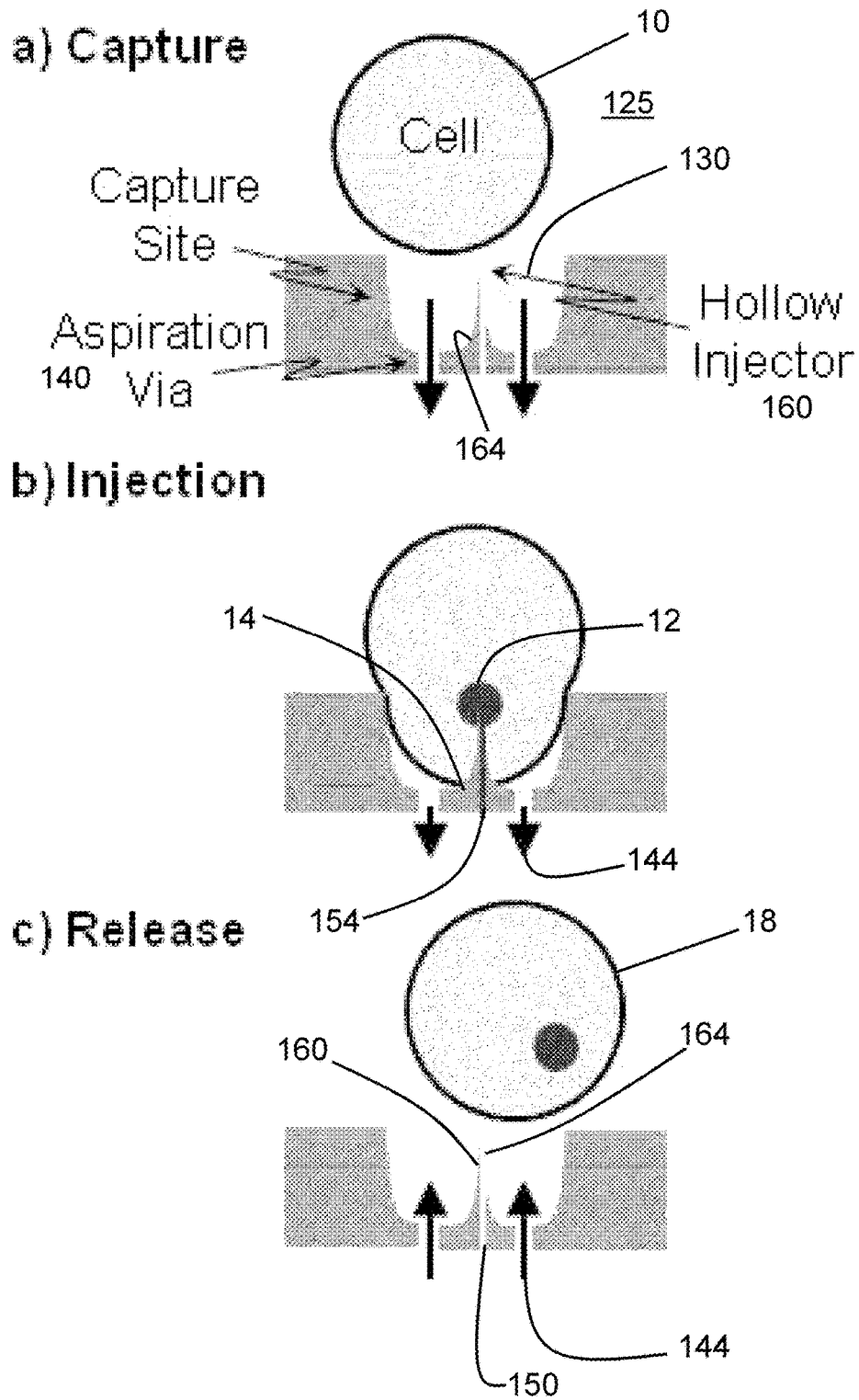
FIG. 3 is a schematic illustration of operation of MEMS-based UHT microinjection device (for single Capture Site within a larger array) according to another embodiment. (a) capture, (b) injection, and (c) release. Arrows within the Aspiration Vias denote flow direction and magnitude, according to one embodiment of the present invention.

FIG. 3 schematically illustrates the UHT microinjection instrumentation operation according to one embodiment of the present invention, which uses a MEMS functional core composed of a 100×100 array of cell Capture Sites with monolithically integrated hollow Injectors. Negative flow through the Aspiration Vias 140 at the bottom of the depression or well 130 draws cells 10 onto the Injectors 160, after which injection 12 commences. Cells 10 are then released by reversing flow through the Vias 140. Aspiration is chosen because it provides capability for rapid capture and release, compatibility with various cell types and sizes, and straightforward implementation. However, the other embodiments are possible using alternate means for capturing and releasing cells. Massive parallelization enables simultaneous capture and injection of thousands of cells/min with minimal need for human or robotic involvement, thus resulting in: a) minimized demand upon the operator; b) reduced instrumentation size, complexity, and cost; and c) throughputs that exceed the current state-of-the-art by many orders of magnitude. Moreover, the monolithically integrated nature of the UHT microinjection device concept is expected to simplify operation and enhance performance significantly relative to other MEMS-based devices demonstrated to date.

FIG. 3 shows a cell 10 being captured within a depression or well 130 of a substrate 122. In some embodiments, the hydrodynamic drag on the cells 10 produced by negative flow (i.e., away from flow channel 125) induces movement of the cells 10. However, in yet other embodiments it may be possible to view the capture of the cell in terms of the pressure differential that causes the negative flow.

After the cell is captured, the outward flow through the aspiration vias is increased (which in some embodiments is an increase in the capturing pressure differential across cell 10) is increased, resulting in a higher drag force (or higher pressure load) and the penetration of injector 160 into the interior of cell 10 through the rupture 14 in the cell wall. Preferably, the lumen 164 of projection 160 is in fluid communication by way of a port 150 with a source 154 of fluid. The pressure within source 154 is increased such that the material 12 enters the captured and held cell 10. Subsequently, fluid flows in vias 140 in a positive manner (i.e, into flow channel 125), which in some embodiments can be viewed as the pressure differential across cell 10 being reversed, with the drag forces on the cell (or the pressure differential across the cell) resulting in movement of the cell out of well 130. Therefore, cell 10 is released and further flushed out of well 130 back into the interior volume 125 of device 120. The cell 18 is modified to contain material 12 then flushed out of device 120 for subsequent use.

Figure 4:
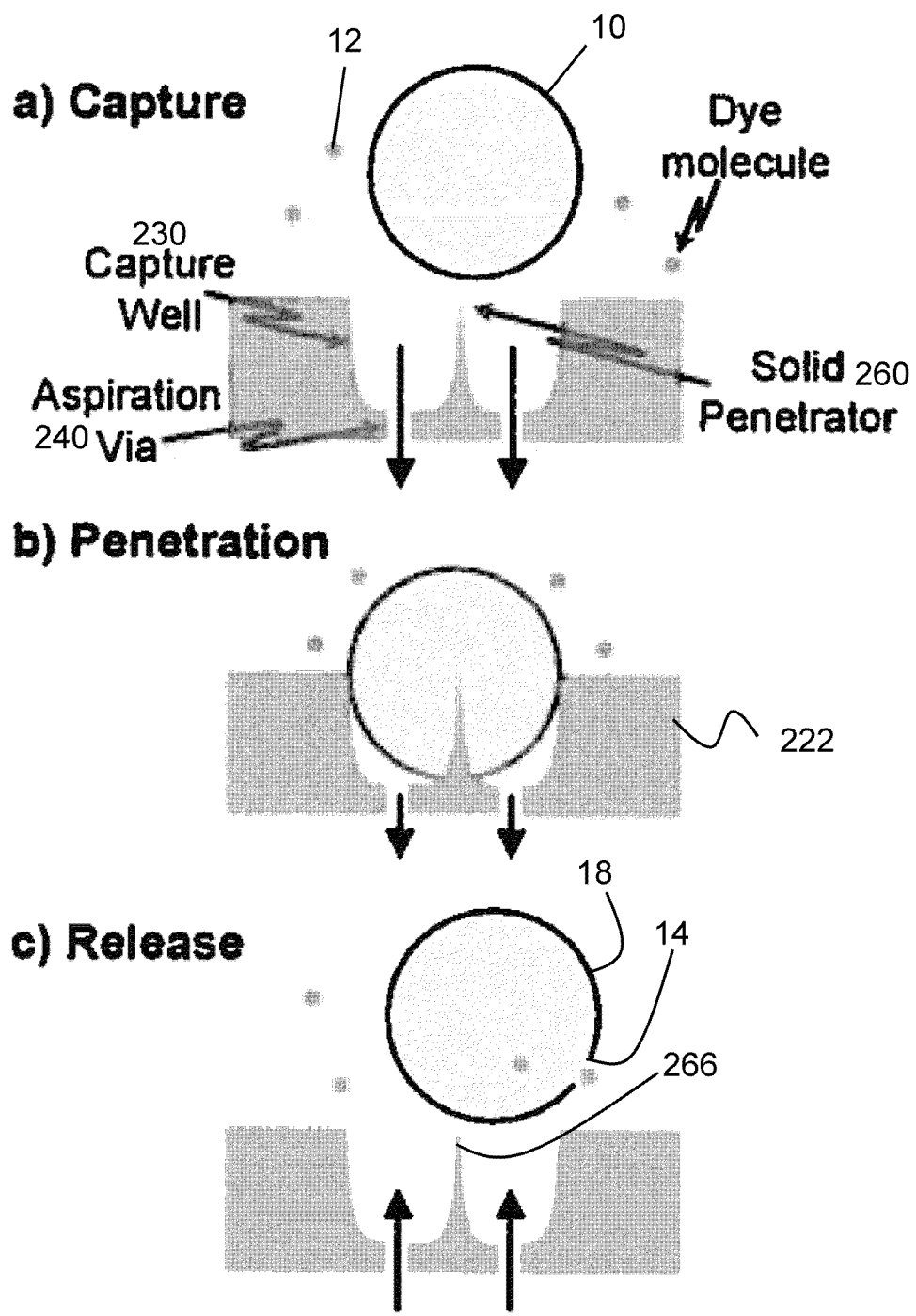
FIG. 4 is a schematic illustration of operation of MEMS-based UHT mechanoporation device (for single Capture Site within a larger array) according to another embodiment. (a) capture, (b) penetration, and (c) release. Arrows within the Aspiration Vias denote flow direction and magnitude, according to one embodiment of the present invention.

The MEMS core for the UHT microinjection device includes a plurality of independent fluidic circuits for aspiration and injection. In yet other embodiments there is a device design in which the injection circuit is eliminated and the hollow Injectors are replaced by solid Penetrators. FIG. 4 schematically illustrates the operation of one example of such an embodiment 125, wherein negative flow through the Aspiration Vias 240 at the bottom of the Capture Well 230 draws cells 10 onto the Penetrators 260, after which the cells 10 are released by reversing flow through the Vias 240. While active injection is optional, the design otherwise mirrors the UHT microinjection device concept 120, thus expediting evaluation of key aspects of feasibility, such as cell capture and puncture 14 efficiency.

Moreover, this embodiment 120 provides utility in and of itself, since it enables cellular manipulation via UHT mechanical membrane disruption, i.e. UHT mechanoporation. In this embodiment 120, the transient nature of cell membrane disruption after puncture and release enables transfection via diffusion-driven influx of exogenous molecules from the surrounding suspension. Alternately, transfection can also be achieved by coating the Penetrators with the desired genetic construct. This approach is advantageous for large screening studies, since different constructs can be spotted across the device array, thus allowing simultaneous evaluation within the same cell population and culture conditions. This, therefore, provides potential for greatly increased throughput, reduced experimental scatter, and enhanced versatility.

FIGS. 5A and 5B shows one of many potential embodiments for implementation of the UHT Mechanoporation concept at the package level, wherein the Device Chip includes through-thickness Inlets 326 and Outlets 328 located away from the Capture Array 230. A Cover Plate 324 containing a microchannel connects the Inlet, Capture Array, and Outlet, thus producing a Flow Channel 325 above the Device Chip (refer to FIGS. 5A and 5B for the following discussion).

The operation procedure begins with filling of the Flow Channel fluidic circuit 325 with buffer, followed by introduction 80-1 of a small aliquot of cells 10 upstream of the package (FIG. 5a). This spatially confined aliquot is then transported 80-2 to the Capture Site Array using positive flow in the Flow Channel, and cells are captured 80-3 using negative aspiration flow (FIG. 5b). Preferably, the flow rate does not cause the penetrators or projections 260 to rupture the cell wall, but simply captures the cells in place. Subsequently, the flow rate is increased in order to permeabilize 80-4 the captured cells, the rupture in the cell wall being the result of the high contact stress between the tip of the projection and the cell wall.

Uncaptured cells are then washed away 80-5 by positive Flow Channel flow, while maintaining low-rate negative aspiration flow to hold captured cells. Finally, captured cells are released 80-6 by positive aspiration flow, and collected using positive Flow Channel flow (FIG. 5c), thus ensuring subsequent analyses are performed on cells that have been permeabilized. In some embodiments, the flow channel fluidic circuit 325 includes a material 12 that enters 80-7 the cells through the rupture sites, thus providing a modified cell 18. A liquoting via computer-controlled syringe pump allows consecutive cycles to be performed automatically, thus providing opportunity for greater throughput, control, and reproducibility.

Figure 6:
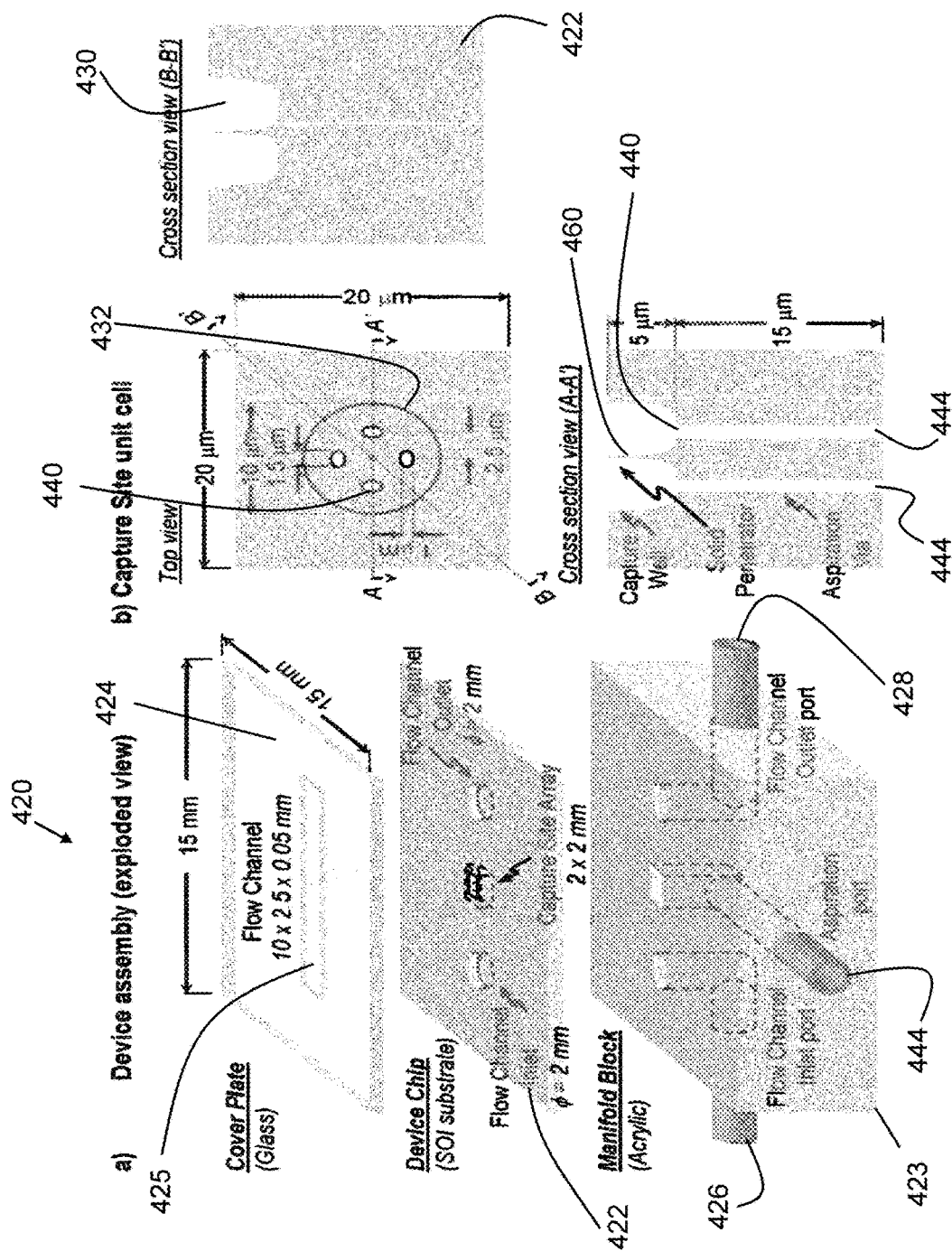
FIG. 6 is a schematic representation of the UHT mechanoporation concept according to another embodiment at the device assembly level: a) Exploded view of Device Assembly; and b) Capture Site unit cell. Each Device Chip contains a 100×100 array of the Capture Site unit cell shown in (b).

FIG. 6 shows one of many potential embodiments for implementation of the UHT Mechanoporation concept at the assembly level, which includes three components: 1) Device Chip 422 containing the Capture Site Array; 2) transparent Cover Plate 424 with Flow Channel 425 that directs cells to the Capture Site Array 430 and then away for collection; and 3) Manifold Block 423 that connects the Aspiration 444 and Flow Channel 426, 428 fluidic circuits to external syringe pumps. It should be noted that Capture Site Array size could be increased and chip size decreased to improve manufacturing efficiency.

Components in the device assembly generally share common perimeters, thus allowing edge alignment, and all are clamped together, thus allowing disassembly for inspection, cleaning, and reuse. The assembly is clamped to the stage of an optical microscope, thus allowing observation of operation through the Cover Plate. Silicone tubing connects the Manifold Block to the syringe pumps, which provide bi-directional fluidic actuation. The syringe pumps can be connected to a computer, thus providing precise control of instrument operation, i.e. flow rates, directions, and actuation sequence.

The Flow Channel in the Cover Plate can be produced by attaching a micromolded polydimethylsiloxane (PDMS) layer with thickness that defines the channel height to a glass slide. The PDMS compliance can provide leak-free, temporary connection of the Cover Plate and Device Chip, although permanent bonding is also possible, and would likely be preferred, such as in those embodiments that serve as the basis of disposable cartridge that would be replaced as needed. The Flow Channel width exceeds that of the Capture Site Array to minimize boundary effects on flow uniformity across the Array, and its height is about five times greater than the nominal size of the cells to be manipulated to minimize potential for clogging. The Manifold Block is fabricated from acrylic using conventional machining techniques. Port dimensions are similar to those on the Device Chip and sufficiently large to minimize pressure drop and simplify fabrication. Acrylic ferrules are press-fit into the port outlets on the lateral faces, thus providing attachment points for the silicone tubing. A PDMS gasket is attached to the upper face for the connection to the Device Chip.

The Device Chip contains a 2 mm×2 mm array of Capture Sites fabricated using bulk silicon micromachining techniques (discussed below). The Capture Site dimensions and their spacing (i.e. pitch) are related to the size of cells to be manipulated. For the 10 μm average diameter THP-1 or K562 (range 7-40 μm) cell lines used for testing, Capture Sites with 10 μm diameter, 5 μm depth, and 20 μm pitch is used, as shown in FIG. 6b, which yields a 100×100 array with $10^4$ total sites. Each Capture Site 430 (or well) contains four 1 μm×1.5 μm elliptical Aspiration Vias 440 (or ports) located at the bottom of the hemispherical Wells. Although elliptically-shaped via (or ports) are shown and described, it is understood that various embodiments contemplate other shapes, including circular shapes or annular rings as examples. These vias provide connection to a common backside port that serves as a reservoir 444 to ensure uniformity of aspiration flow across the array. Use of multiple Vias in each Capture Site provides uniform tension on the cell membrane to facilitate penetration, as well as redundancy in the event of clogging. However, yet other embodiments of the present invention contemplate capture sites having as few as one Via, or more than four Vias. Integrated solid Penetrators 460 are situated at the center of each site and have conical geometry with sub-μm tip 466 diameter, ~1-2 μm base 462 diameter, and ~5 μm length. When coupled with the high strength of silicon, this geometry provides mechanical reliability and minimizes penetration force, thus minimizing deformation and stress on the cell.

For the given device geometry, 5 v % suspensions yield at least one cell per unit volume above the Capture Site, thus permitting assumption of Newtonian behavior. Moreover, since the Aspiration Vias collectively act as a membrane filter with small pore size, and flow rate is low (i.e. 5 pL/s/Via, which is sufficient to exchange the entire volume above a Capture Site unit cell within 1 s), flow can be assumed to be laminar and governed by Poiseuille law (adjusted for elliptical Via cross section). Based on these parameters, pressure drop is estimated to be 1.3 kPa.

The 2 mm×2 mm Capture Site Array is defined in a 20 μm thick silicon membrane with lateral dimensions of 2.5 mm×2.5 mm. Each capture site (or well) 430 has a boundary shape 432 that is adapted and configured to support a portion of a cell 10. In some embodiments, boundary shape 432 is less than the diameter of the cell being tested, such that a portion of the cell sits on top of substrate 422 and does not enter well 430. The lateral dimensions of the membrane exceed those of the Array so that boundary effects do not compromise flow uniformity. The membrane thickness is chosen to match that of the UHT microinjection devices and minimize pressure drop. The expected 1.3 kPa pressure differential is well below the 6600 kPa failure pressure estimated for a comparable solid membrane (i.e. without perforation), thus providing margin for accommodating strength reduction produced by stress concentration at the Aspiration Vias.

Figure 7:
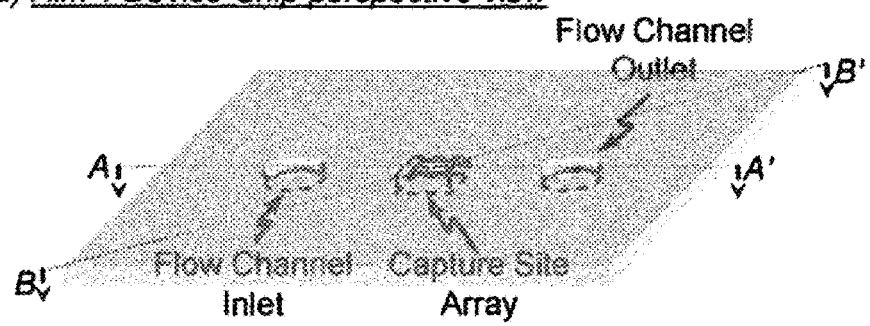
FIG. 7 shows an abridged microfabrication process according to another embodiment for UHT mechanoporation device according to one embodiment of the present invention. Note: Although the Device Chip contains a 100× 100 array of Capture Sites, only one site is shown for the sake of clarity. It is appreciated that this array is one specific example, and the apparatus and methods disclosed herein are scalable to larger or smaller arrays. (a) perspective view, (b) cross-section view (A-A'), and (c) cross-section view (B-B').
Figure 7:
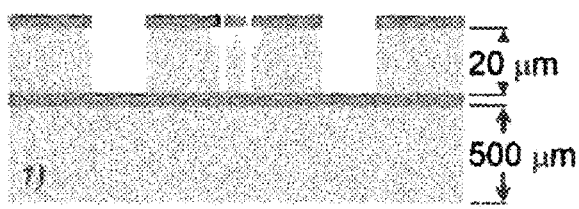
Figure 7:
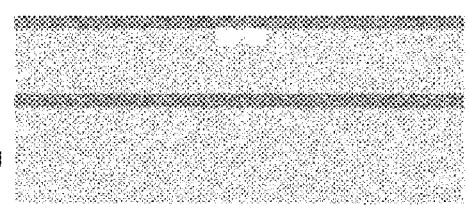
Figure 7:
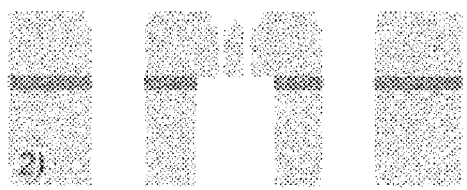
Figure 7:
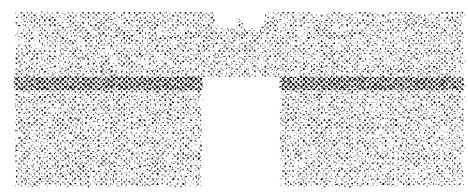

As shown in FIG. 7, the UHT mechanoporation device is fabricated using a single silicon-on-insulator (SOI) substrate with 20 μm Si device layer, 2 μm buried $SiO_2$ layer (BOX), and 500 μm Si handle layer. The front side is coated with a 1 μm $SiO_2$ etch mask using PECVD and lithographically patterned with the Aspiration Vias and Flow Channel Inlet/Outlet features. These features are then transferred to the oxide layer using dry etching. The Si device layer is then isotropically dry etched to produce solid Penetrators with sharp tips located in the center of roughly hemispherical Capture Wells. Anisotropic dry etching using Si DRIE extends the Aspiration Vias to the BOX layer and the frontside mask oxide is removed by wet etching. The large Aspiration and Flow Channel Inlet/Outlet ports are lithographically patterned on the backside and extended to the BOX layer using Si DRIE. The BOX layer is dry etched. In some embodiments, the devices are subjected to a short thermal oxidation step to produce a 50-100 nm coating of $SiO_2$ on exposed surfaces, to allow use of standard surface passivation techniques to minimize non-specific binding and potential for fouling.

Figure 8:
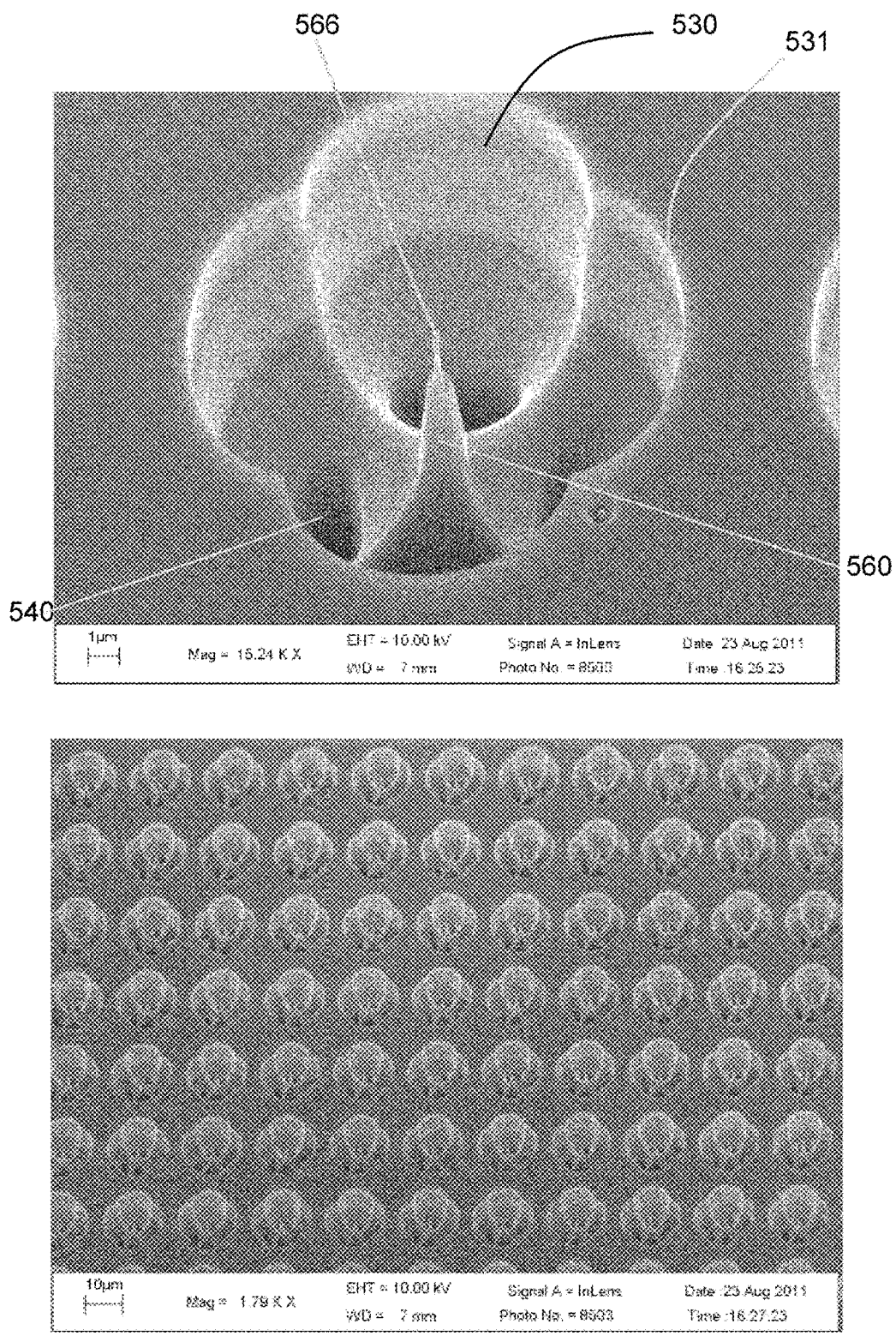
FIG. 8 shows scanning electron micrographs of a fabricated UHT mechanoporation device according to another embodiment with capture wells: (Top) Single Capture Site with 200 nm diameter monolithically integrated solid Penetrator; and (Bottom) Lower magnification view of a portion of the Capture Site array.
Figure 9:
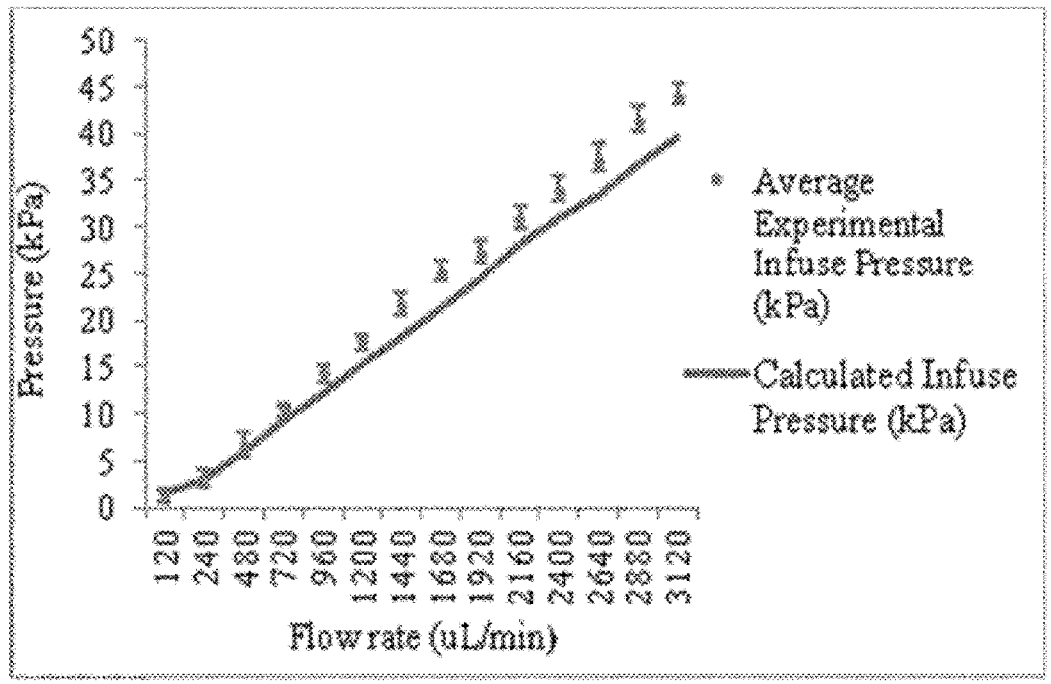
FIG. 9 is a graphical representation showing plots of experimentally measured and analytically predicted pressure drops as function of applied aspiration flow rate for positive aspiration flow (i.e. infusion) of DI water through the UHT mechanoporation device. The data reported for measured pressure drop represents an average of several experiments on the same device, and the error bars represent standard deviation.
Figure 10:
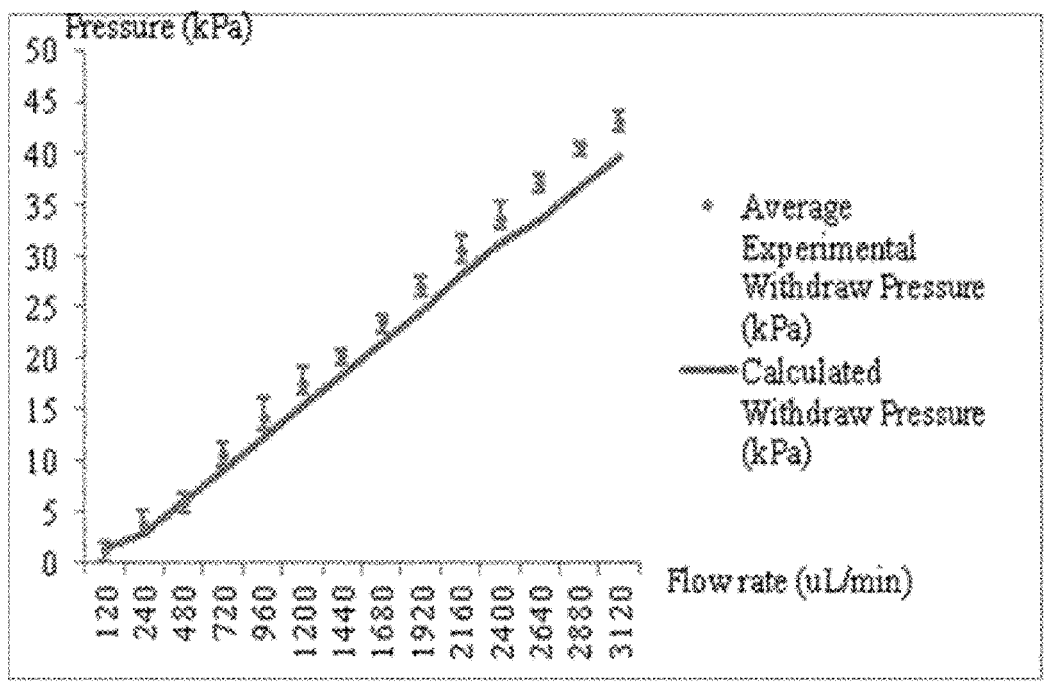
FIG. 10 is a graphical representation showing plots of experimentally measured and analytically predicted pressure drops as function of applied aspiration flow rate for negative aspiration flow (i.e. withdrawal) of DI water through the UHT mechanoporation device. The data reported for measured pressure drop represents an average of several experiments on the same device, and the error bars represent standard deviation.

As shown in FIG. 8, the aforementioned fabrication process produces UHT Mechanoporation devices with appropriate dimensions and geometry. Acceptable uniformity across the Capture Site Array is achieved. In the top of FIG. 8, a close up scanning electron micrograph of a capture site 530 shows that the boundary shape of the capture site comprises an overlapping of four larger elliptical shapes. The four smaller elliptical vias or ports 540 can be seen at the bottom of each of the larger elliptical shapes. Note that the size of the larger elliptical shape 531 is adapted and configured to leave a projection 560 within the well 530 after the four larger elliptical volumes 531 have been removed from substrate 522. As shown in FIGS. 9 and 10, data from positive and negative aspiration flow studies with DI water confirm the devices' ability to withstand pressure drops well in excess of those required for normal operation (~1.3 kPa, as detailed earlier).

Preliminary characterization of cell permeabilization using the UHT mechanoporation device has been performed using manual actuation of the aspiration circuit and cell counting by manual hematocytometric and automated flow cytometric approaches. Test samples were prepared in a single device operation cycle by: 1) pipetting 50 k live K562 cells onto the device; 2) capturing cells via negative aspiration flow; 3) washing excess uncaptured cells with pipetting; 4) permeabilizing captured cells using slightly greater negative aspiration flow pulse; 5) releasing permeabilized cells using positive aspiration flow; and 6) collecting released cells by pipette. At least 1 such cycle was performed in each experiment, with up to 3 independent cycles completed in some experiments. Addition of vital dye to the collected cell suspensions enabled quantification of permeabilization (trypan blue & propidium iodide, for hematocytometric & flow cytometric counting, respectively). Also prepared were: 1) Background samples—cells collected, centrifuged, and vortexed; 2) Negative Control samples—cells pipetted onto device surface, held quiescent for 1 min, collected, and then processed similarly to Test samples; and 3) Positive Control samples—similar to Background samples, but with addition of detergent NP40 to disrupt the cell membrane.

Figure 11:
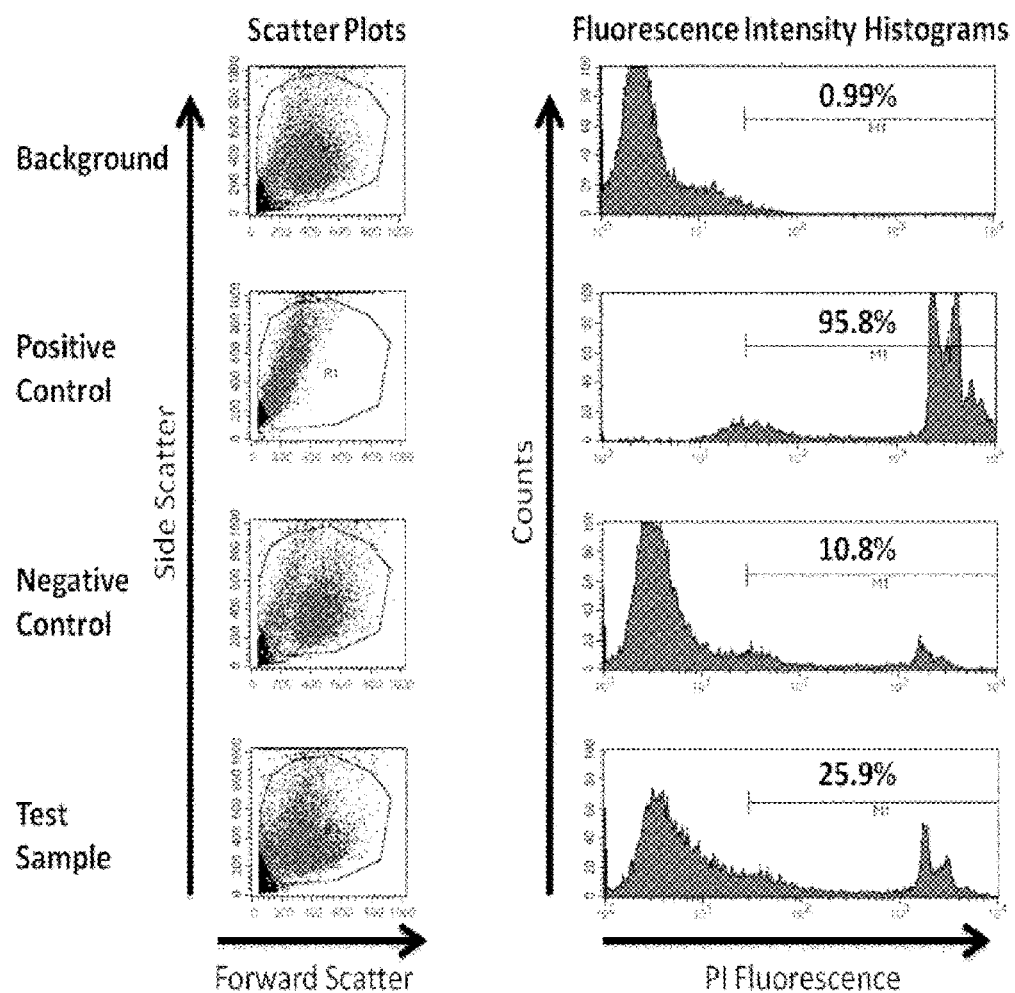
FIG. 11 shows the flow cytometry results for UHT mechanoporation device: (Left) Scatter plots (cell size/granularity) showing intact membrane cells occupying larger population in the center of the plots and cells with disrupted membranes (punctured) occupying population near the Side Scatter axis; (Right) Histogram showing overall puncture efficiency of ~15% above Negative Control using sample consisting of combined cells from 15 cycles (percent dye positive cells indicated on each plot). This is one example only. Higher efficiencies may occur with modified device design and/or operational parameters.

Results from hematocytometric counting are shown in Table 1 and indicate test sample cell permeabilization efficiencies up to 50% greater than the Background and Negative Control for single cycle experiments. Results from multiple cycle experiments indicate that efficiency can decrease in some situations. Results from flow cytometric counting of cells pooled from 15 cycles are shown in FIG. 11 and indicate lower overall permeabilization efficiency of ~15% above Negative Control.

TABLE 1

Permeabilization efficiency for K562 cells using manual hemotocytometric counting.

| Samples | Cycles | | % Dye Positive |
|---|---|---|---|
| Background | N/A | | 9.8 |
| Negative Control | N/A | | 10.8 |
| Positive Control | N/A | | 99.9 |
| Test 1 | 2, combined | cycle 1 + 2 | 62.7 |
| Test 2 | 2, separate | cycle 1 | 57.1 |
| | | cycle 2 | 18.1 |

Figure 12:
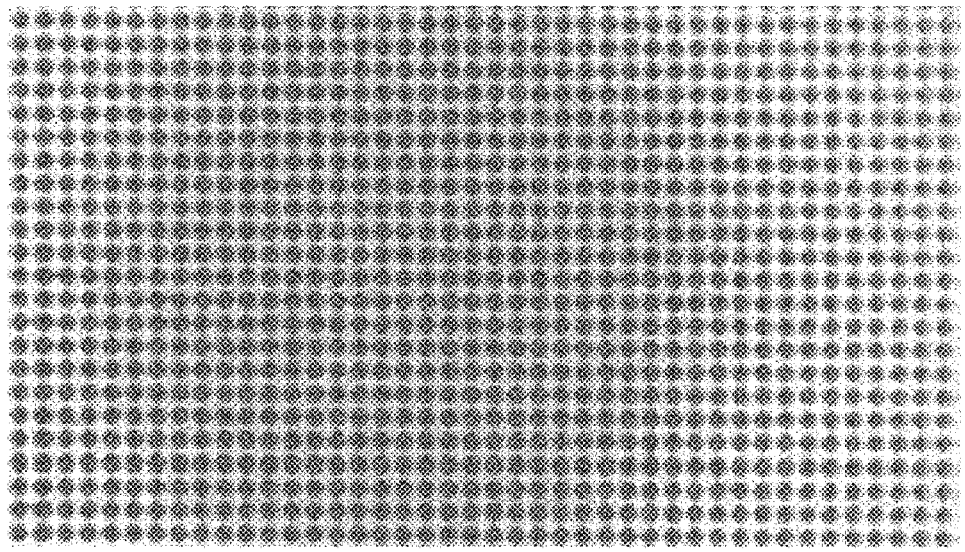
FIG. 12. (a)-(d) show fluorescence microscope images showing progression of cell capture with time during the MEF cell suspension experiment (specific time points for each image are indicated on the pressure plot of (e) by arrows). Note: Use of both top- and bottom-side illumination allowed visualization of capture sites due to light transmission through the aspiration vias, which are visible as periodically arrayed bright spots in the uncovered sites. (e) shows the plot of pressure drop vs. time for UHT mechanoporation experiment with MEF cells, as well as control experiment with buffer alone according to one embodiment of the present invention.
Figure 12:
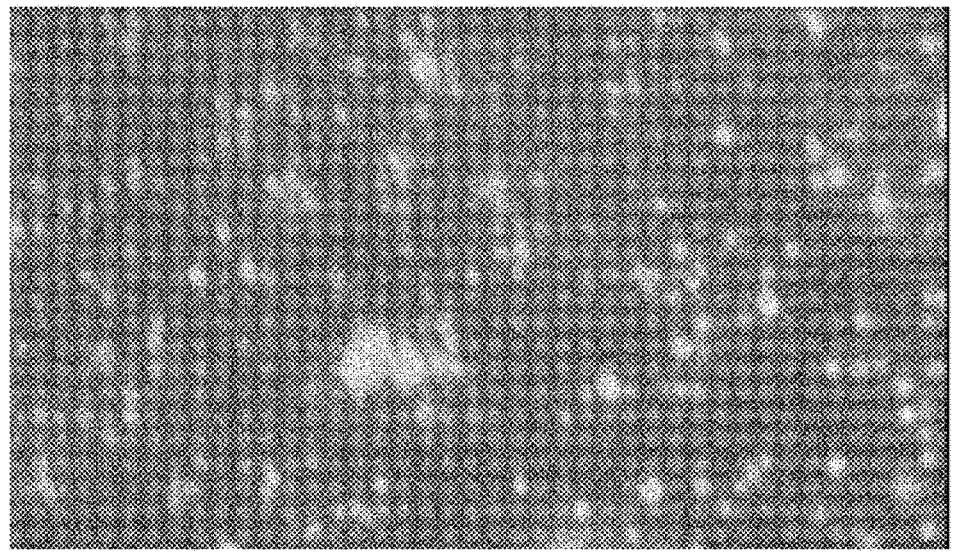
Figure 12:
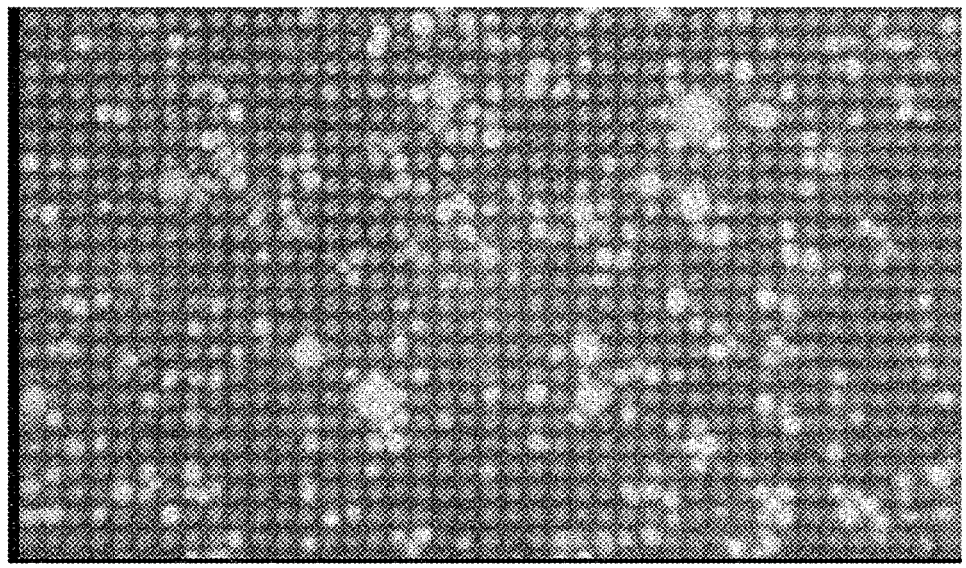
Figure 12:
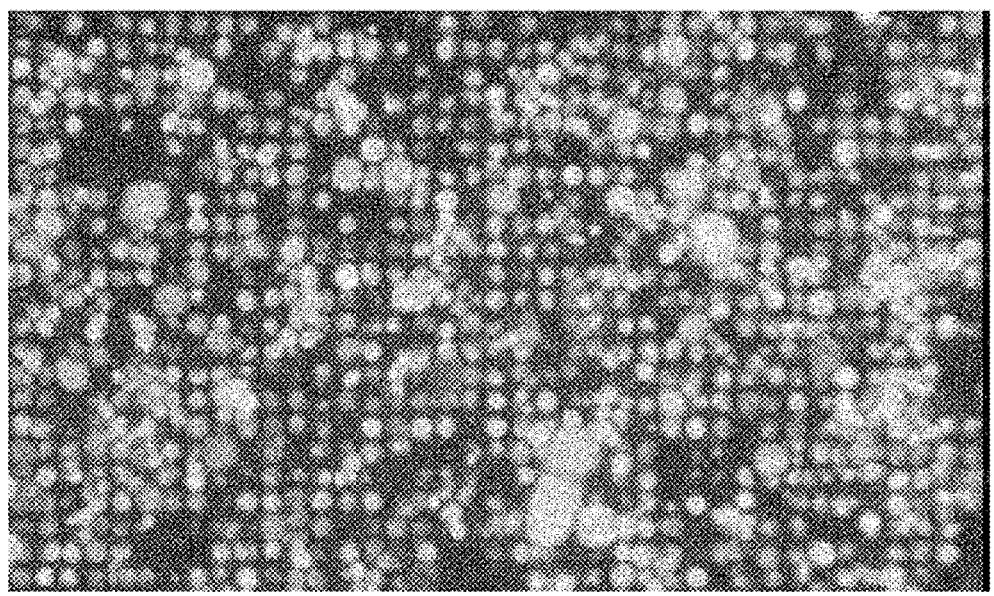
Figure 12:
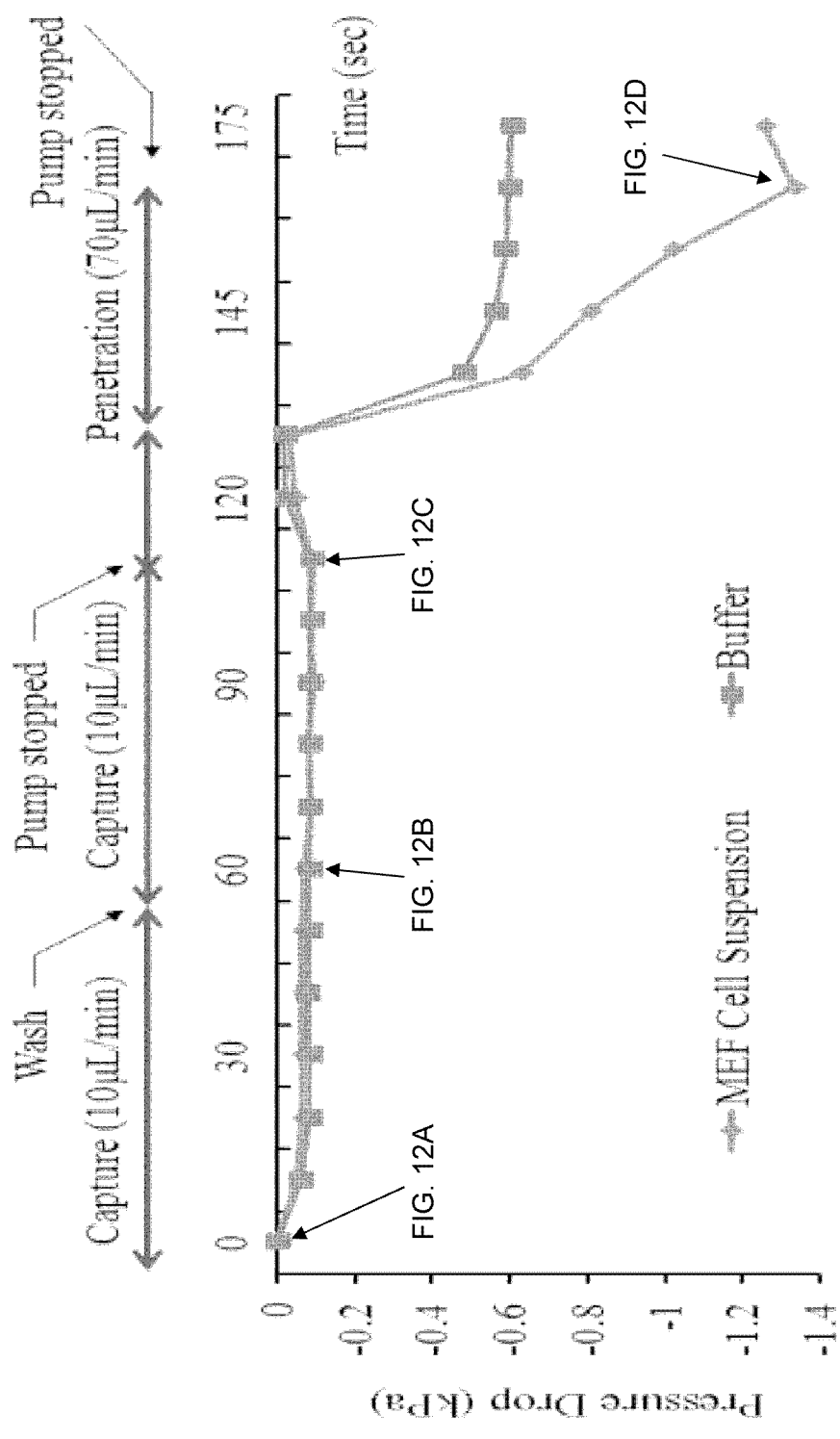

In another example, fluorescently labeled mouse embryonic fibroblast (MEF) cells were used. The cells were introduced by manual pipetting (50 k cells in 20 μL), followed by initiation of negative aspiration flow under flow rate controlled conditions similar to those previously discussed. As shown in FIG. 12, an aspiration flow rate of 10 μL/min was imposed for the capture step, and manual washing by pipetting was used to remove uncaptured cells at the mid-point of the step. The pump was then stopped and a higher flow rate of 70 μL/min was imposed for the penetration step. FIG. 12 also shows pressure data from a control experiment using buffer alone.

As evidenced in both the pressure plot and the accompanying fluorescence images (FIGS. 12a-d), only limited numbers of cells were captured during the 110 s capture step. The capture step in our original studies was 30 s, and some embodiments use longer capture times and/or higher flow rates. The increasing pressure drop with time observed during the penetration step is likely caused by increasing capture site occupation with time.

Figure 13:
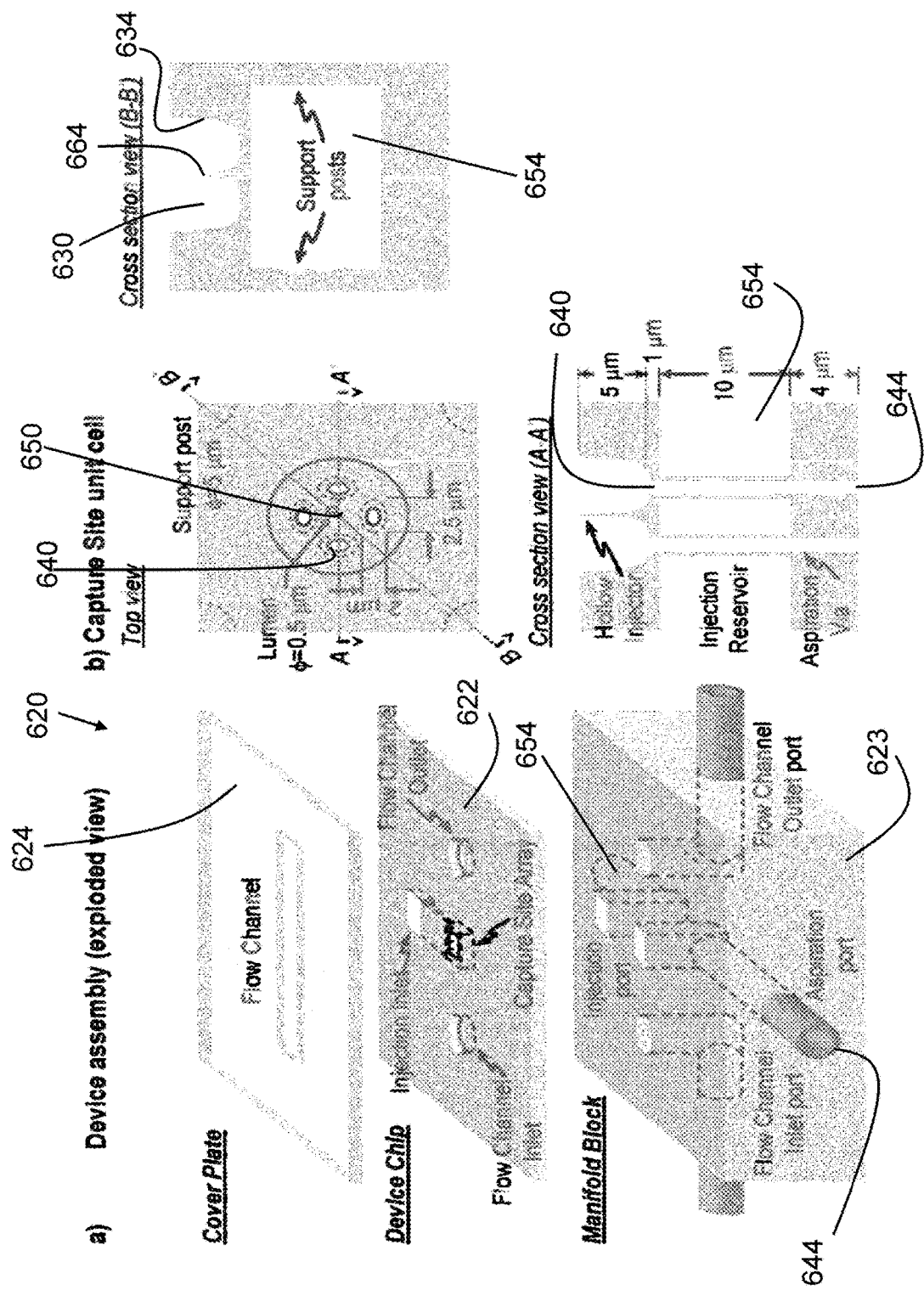
FIG. 13 is a schematic representation of the UHT microinjection concept according to another embodiment at the device assembly level: a) Exploded view of Device Assembly; and b) Capture Site unit cell. Each Device Chip contains a 100×100 array of the Capture Site unit cell shown in (b).
Figure 14:
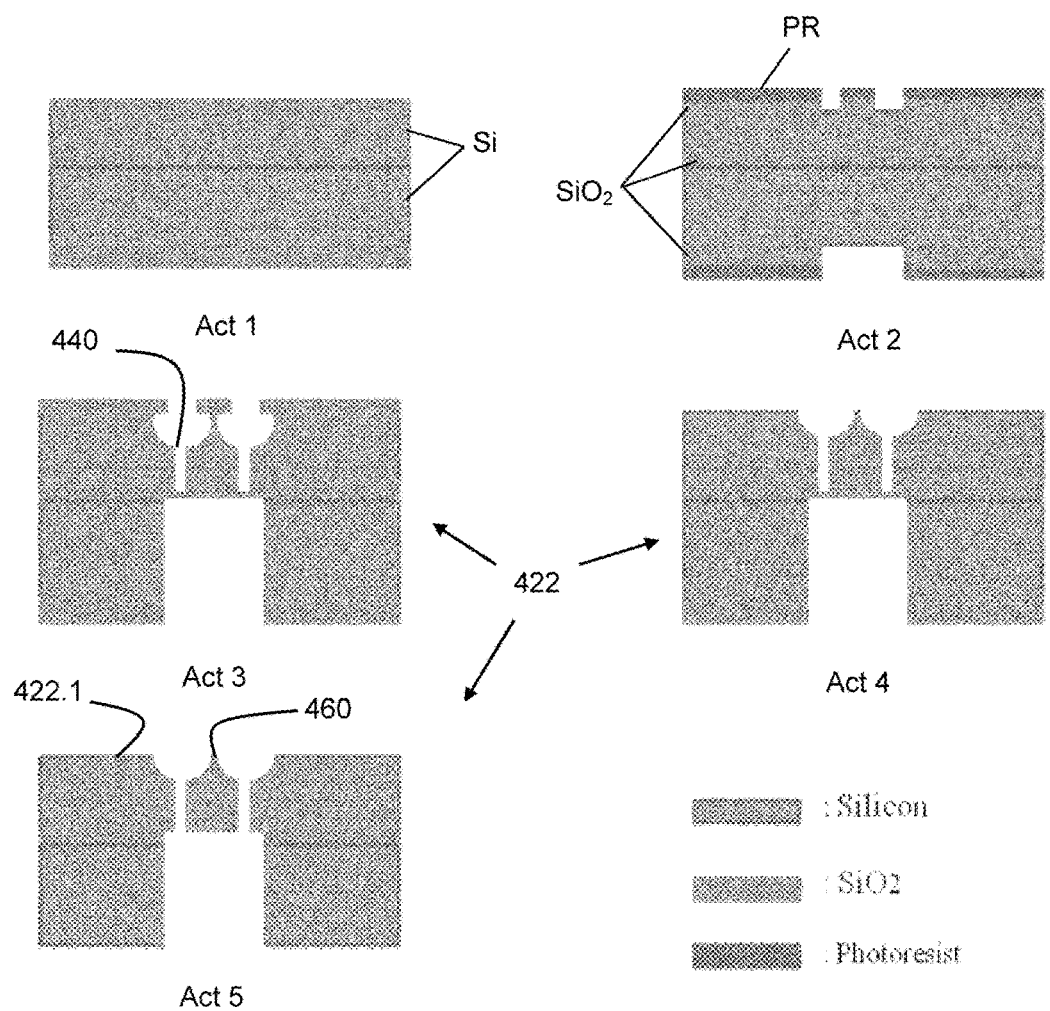
FIG. 14 shows the device microfabrication process flow according to another embodiment. Only one Capture Site is shown for the sake of clarity.
Figure 15:
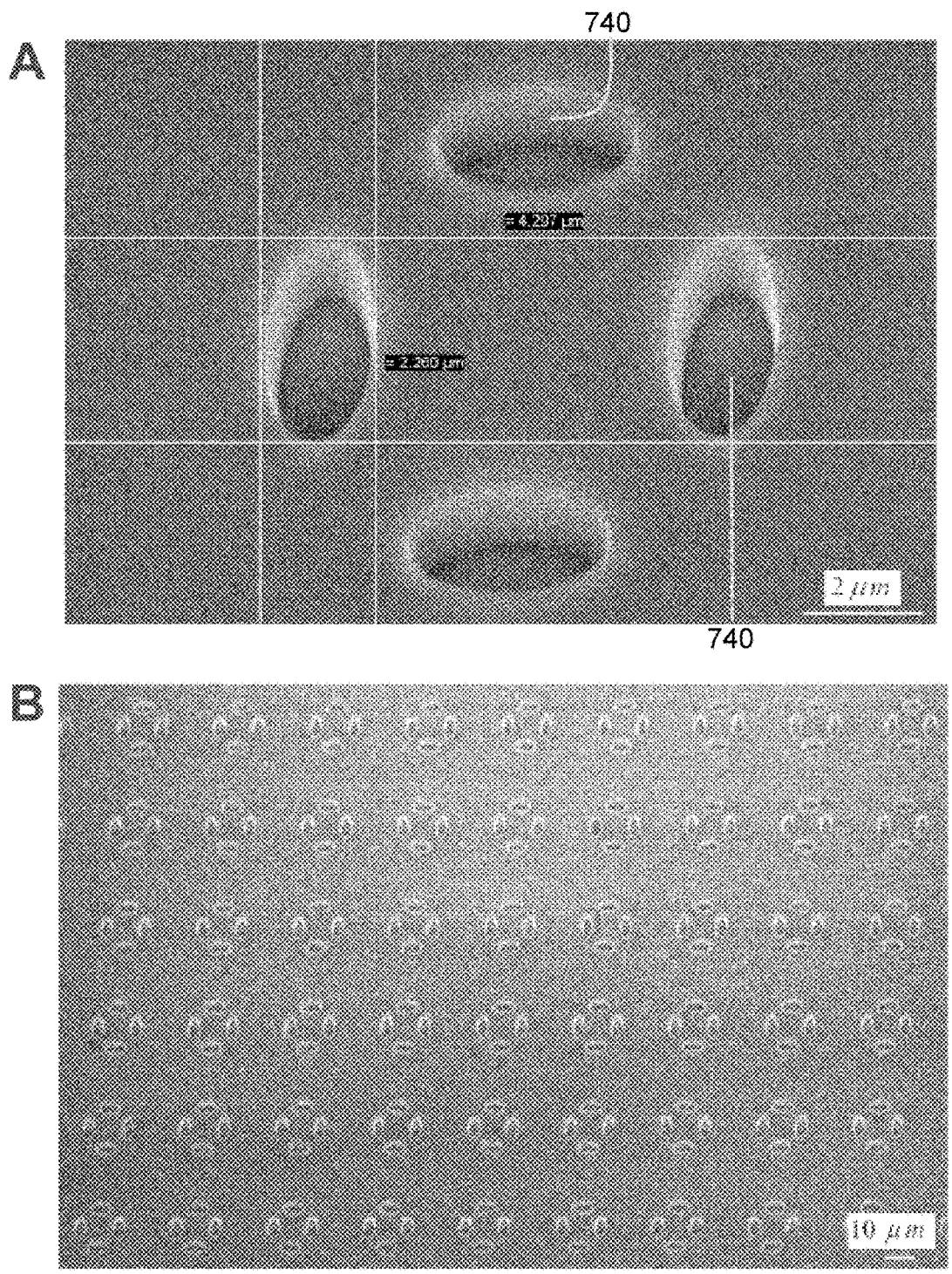
FIG. 15 shows the SEM images of elliptical via patterns. (a) Four elliptical vias to create single capture well and Solid Penetrator later; (b) Lower magnification view of a portion of the elliptical vias array.
Figure 16:
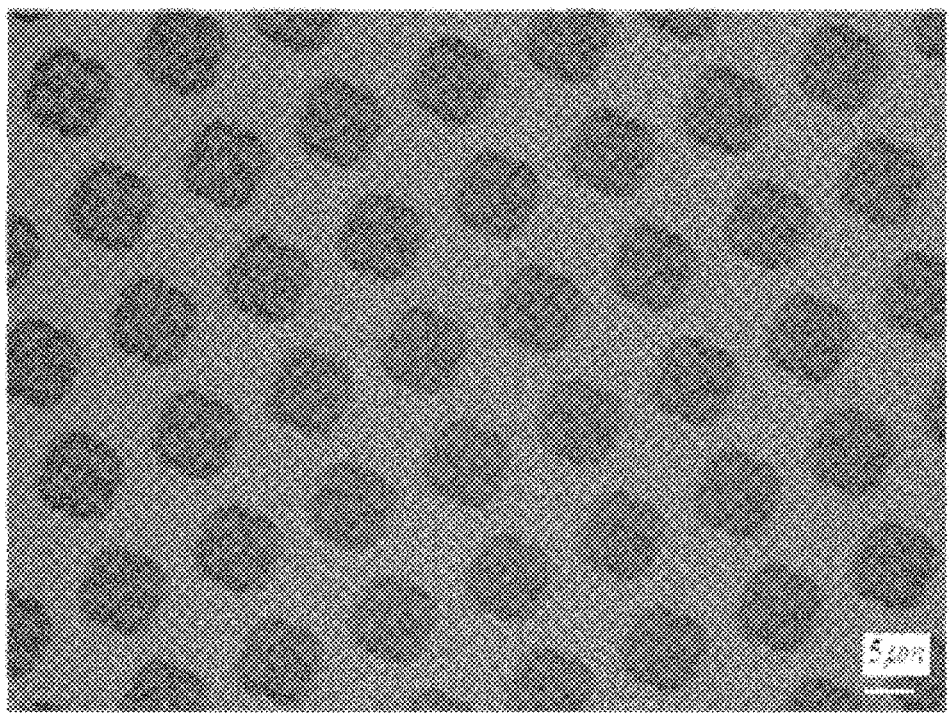
FIG. 16 shows the optical microscope image of a portion of the 100 by 100 capture site array after isotropic etching.
Figure 17:
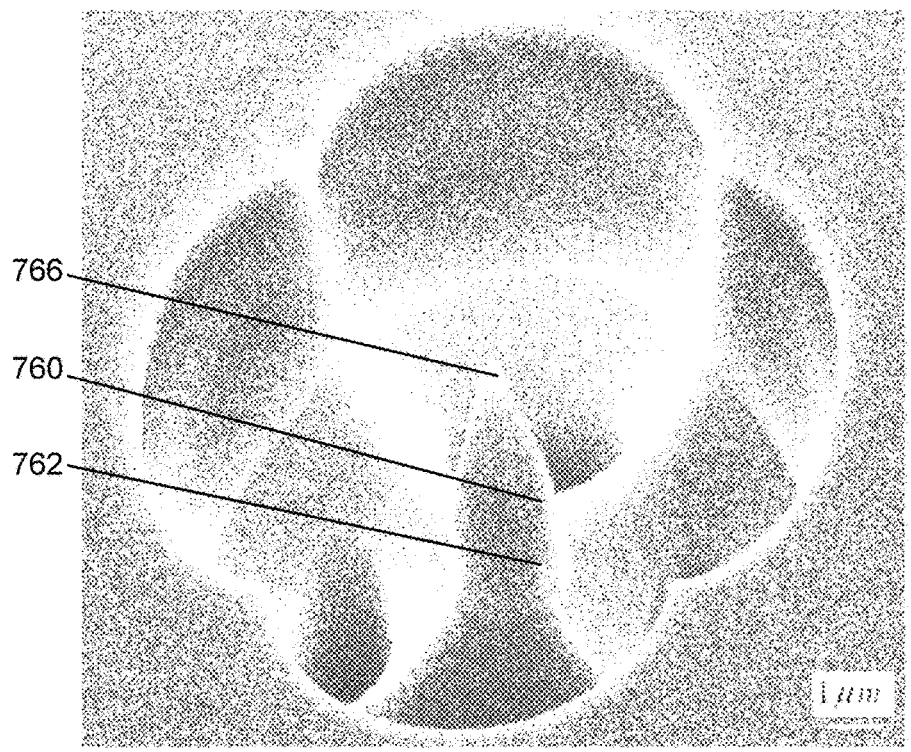
FIG. 17 shows SEM images of capture wells and solid penetrators after Cl2 etching. (a) Single capture well with monolithically integrated Solid Penetrator; (b) Higher magnification view and measurement of the single Solid Penetrator tip; (c) Higher magnification view and measurement of the single Solid Penetrator passivation wildest part; (d) Lower magnification of a portion of the 100×100 capture site array.
Figure 17:
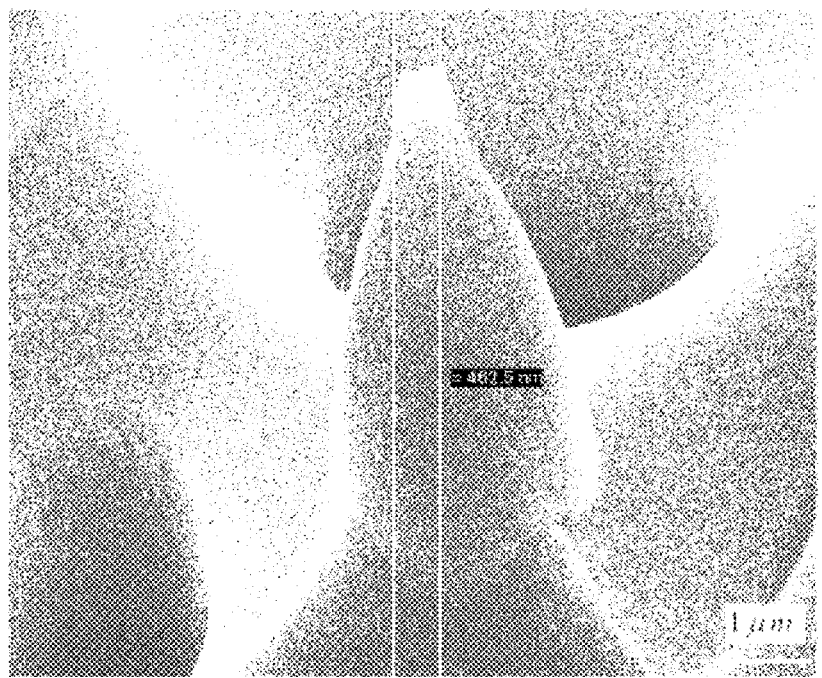
Figure 17:
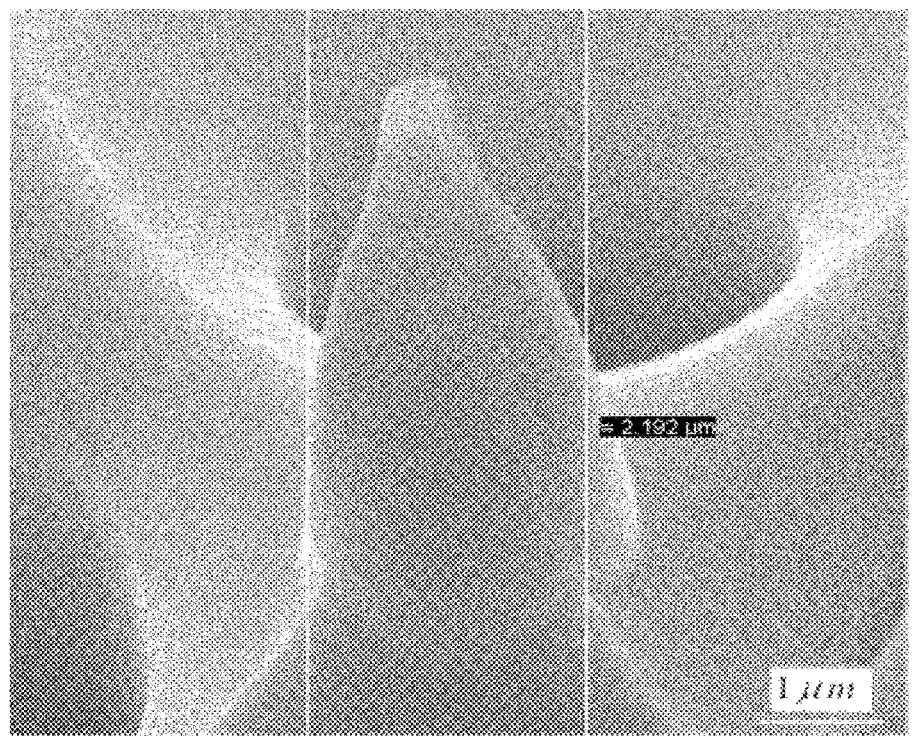
Figure 17:
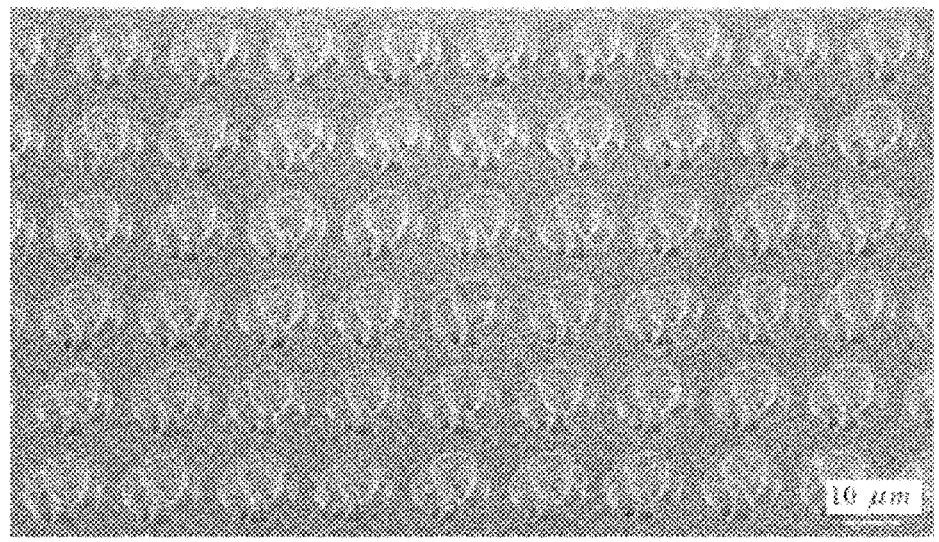
Figure 18:
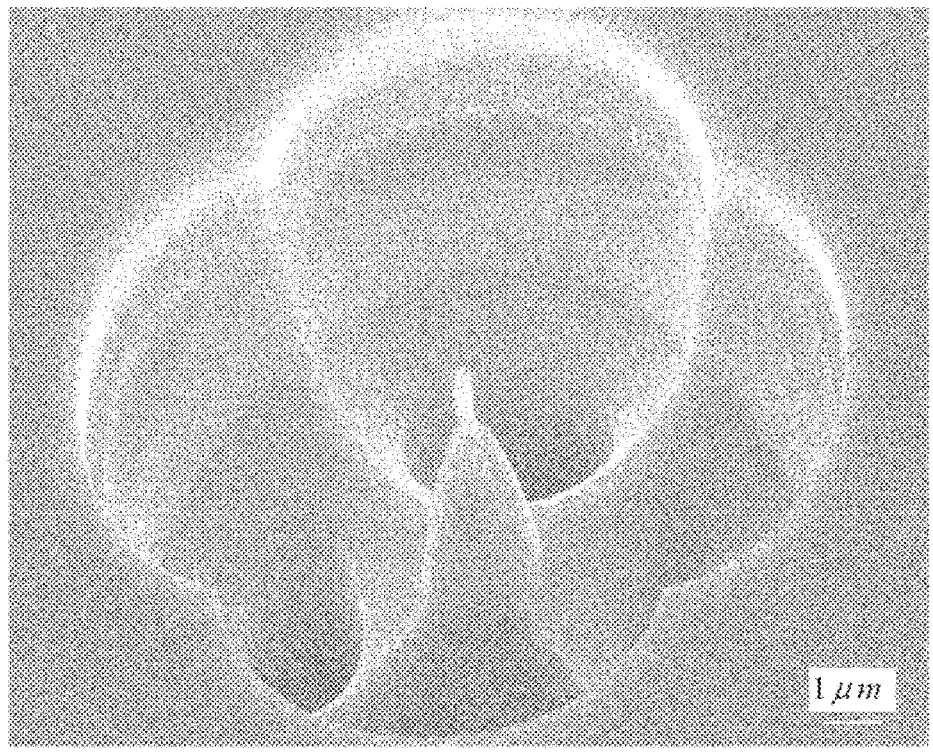
FIG. 18 shows SEM images of capture wells and Solid Penetrators after CL2 passivation removal dry etching. (a) Single capture well with monolithically integrated Solid Penetrator; (b) Higher magnification view of the single Solid Penetrator, with about 342 nm by 928 nm sharp tip; (c) Lower magnification of a portion of the 100×100 capture site array.
Figure 18:
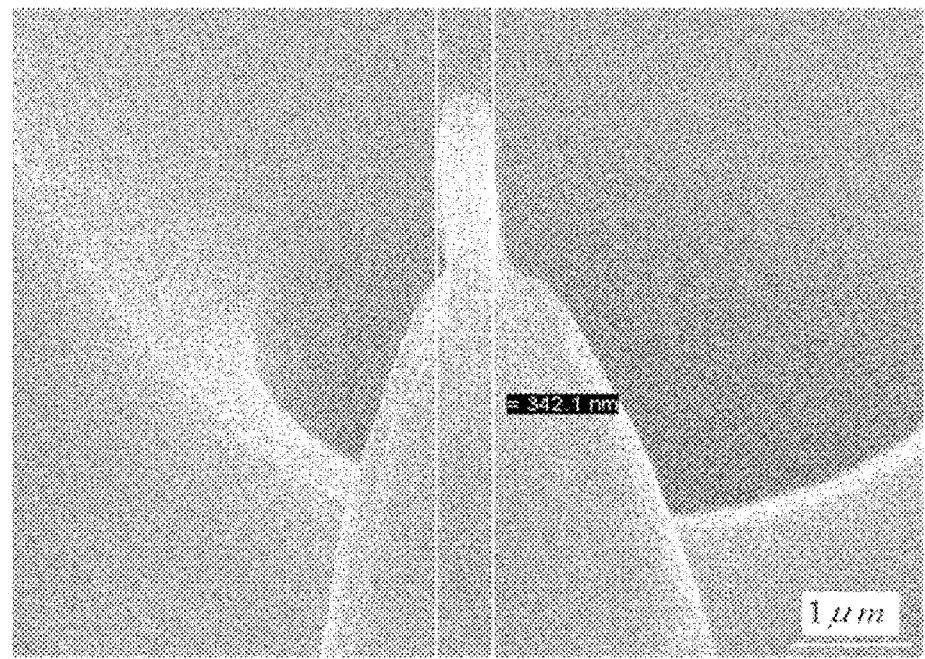
Figure 18:
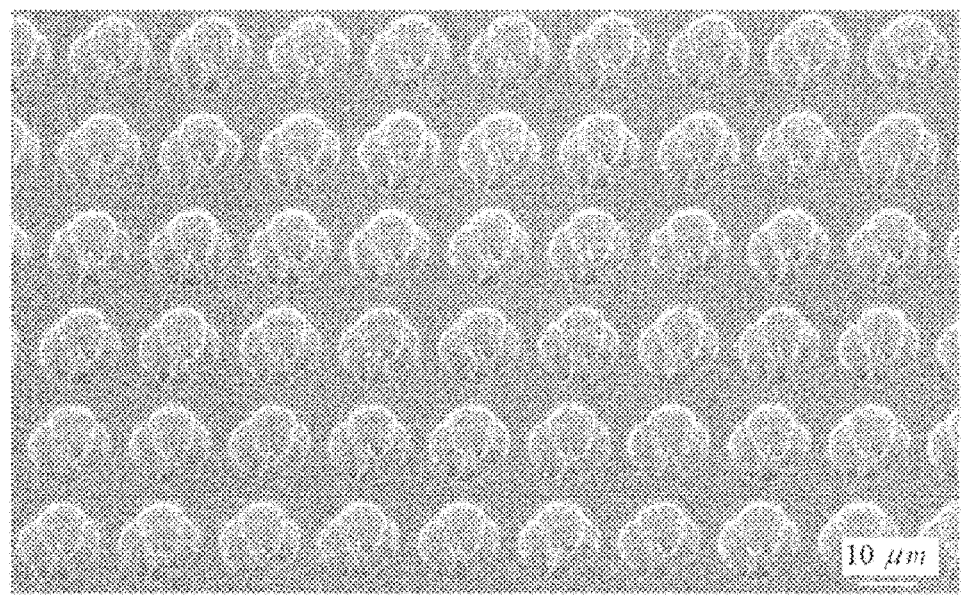
Figure 19:
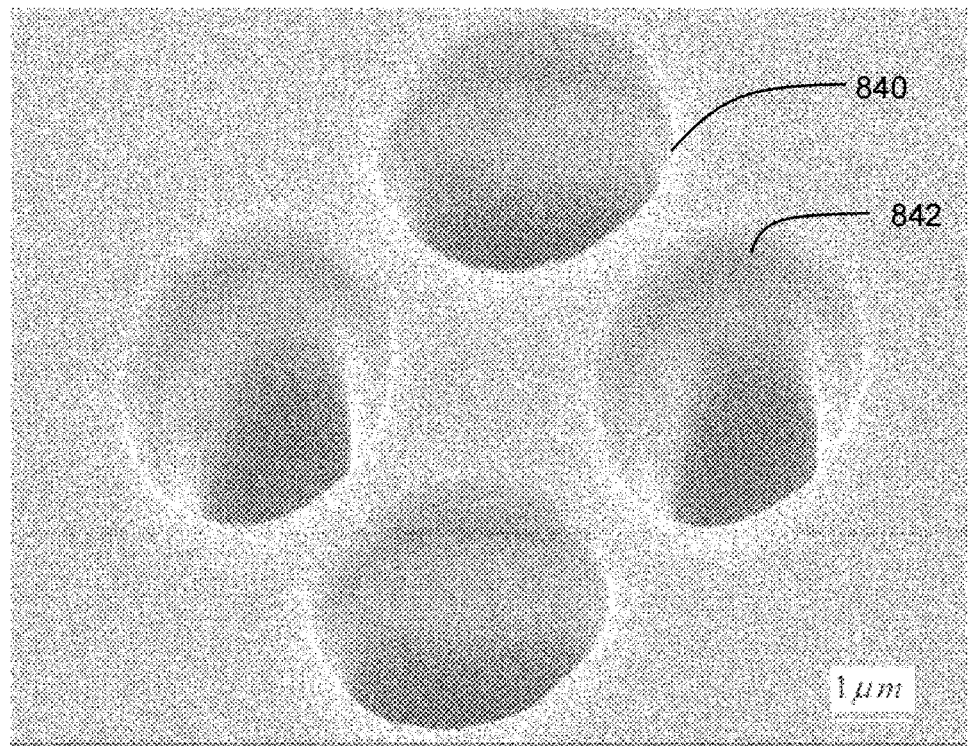
FIG. 19 shows SEM images from backside of chip device, (a) Four vias within a single capture site; (b) Lower magnification view of a portion of the 100×100 vias array; (c) View of backside aspiration ports defined within the handle layer of substrate.
Figure 19:
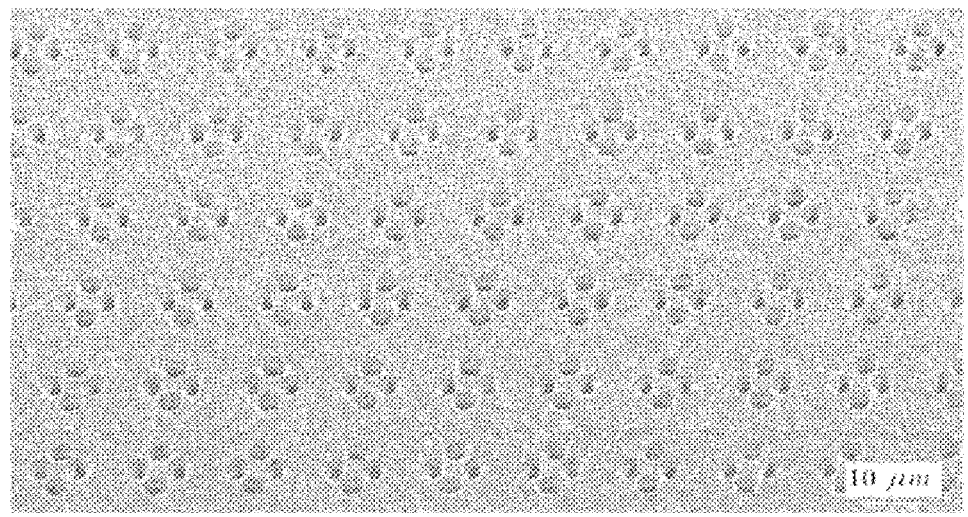
Figure 19:
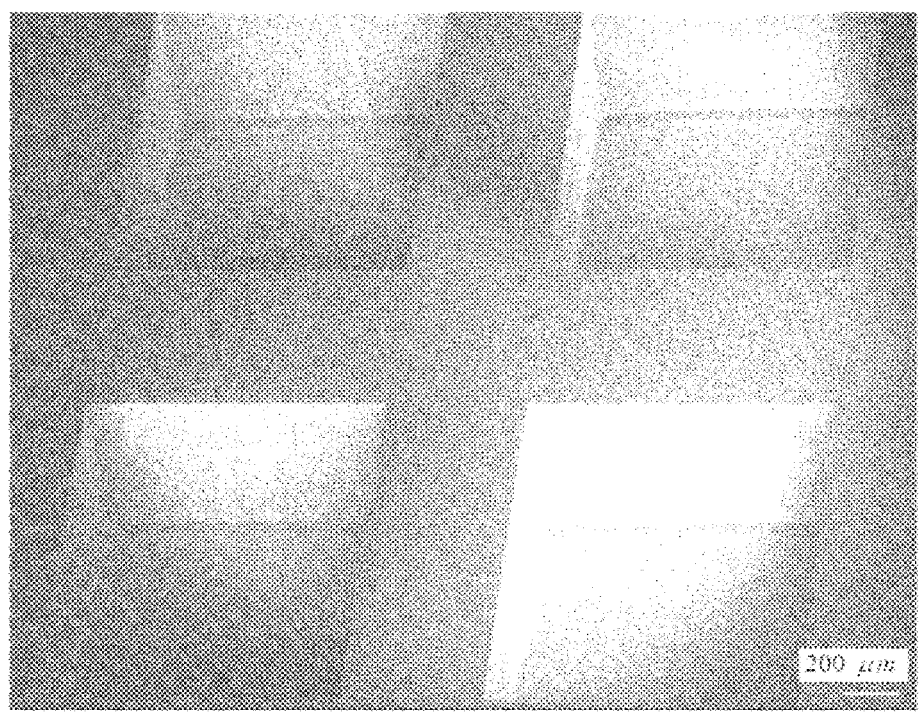
Figure 20:
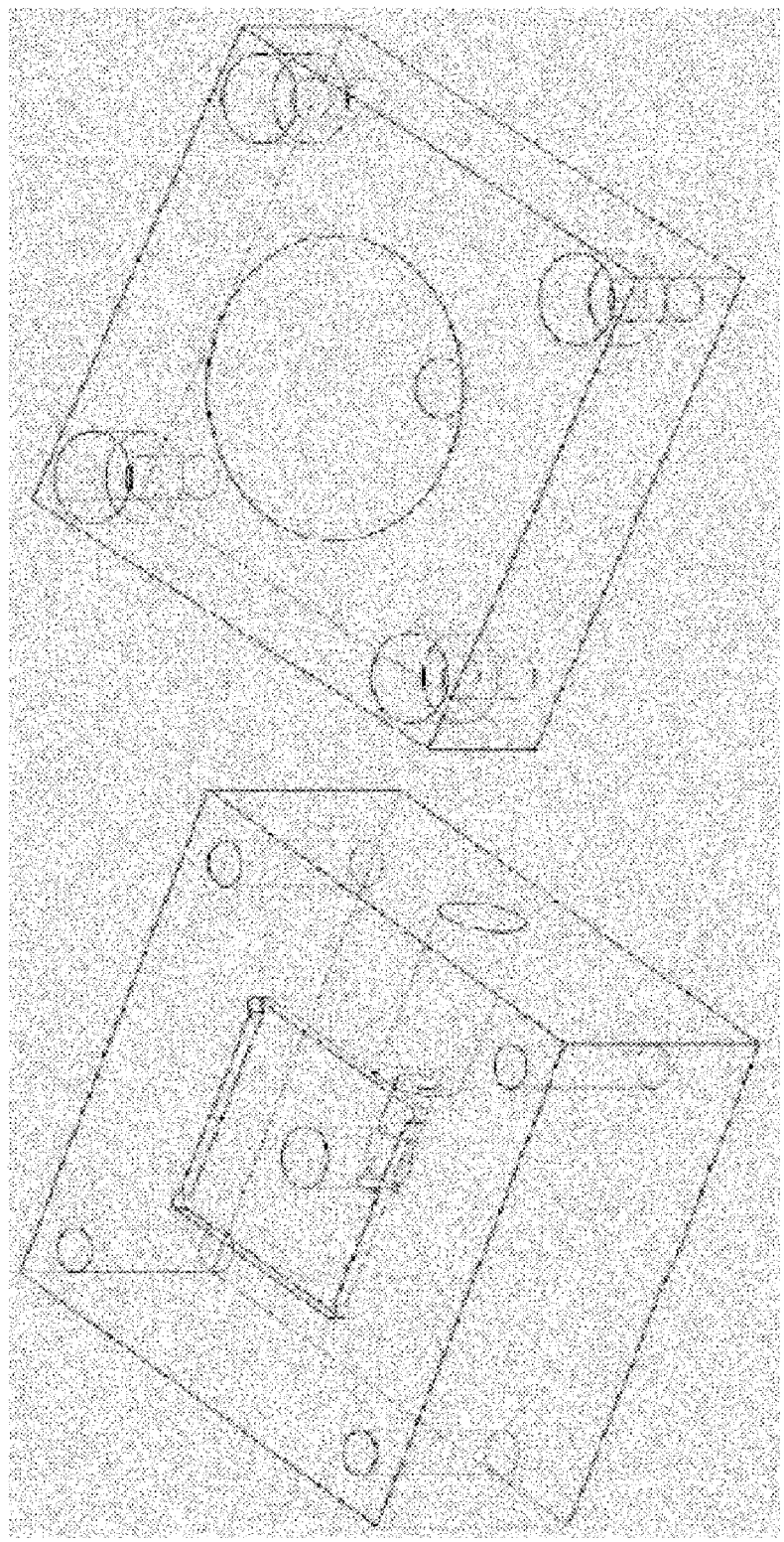
FIG. 20 is a schematic representation of the fixture set. (Left): bottom part of the fixture set, holding device chip in the middle reservoir. (Right): top part of the fixture set.
Figure 21:
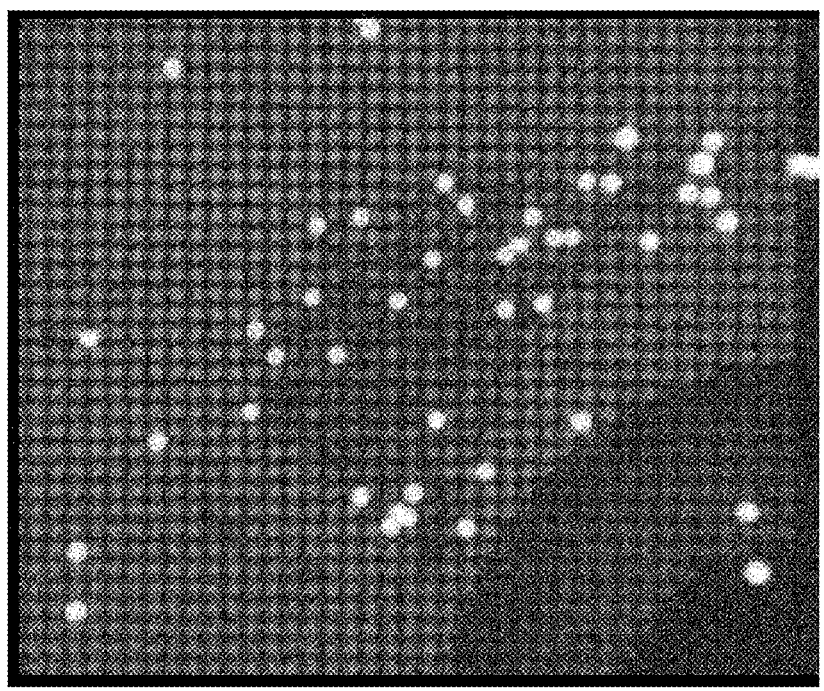
FIG. 21 shows fluorescence images of: (a) bubbles being trapped underneath capture well arrays and (b) bubbles being completely eliminated from capture well arrays after rigorous flushing.
Figure 21:
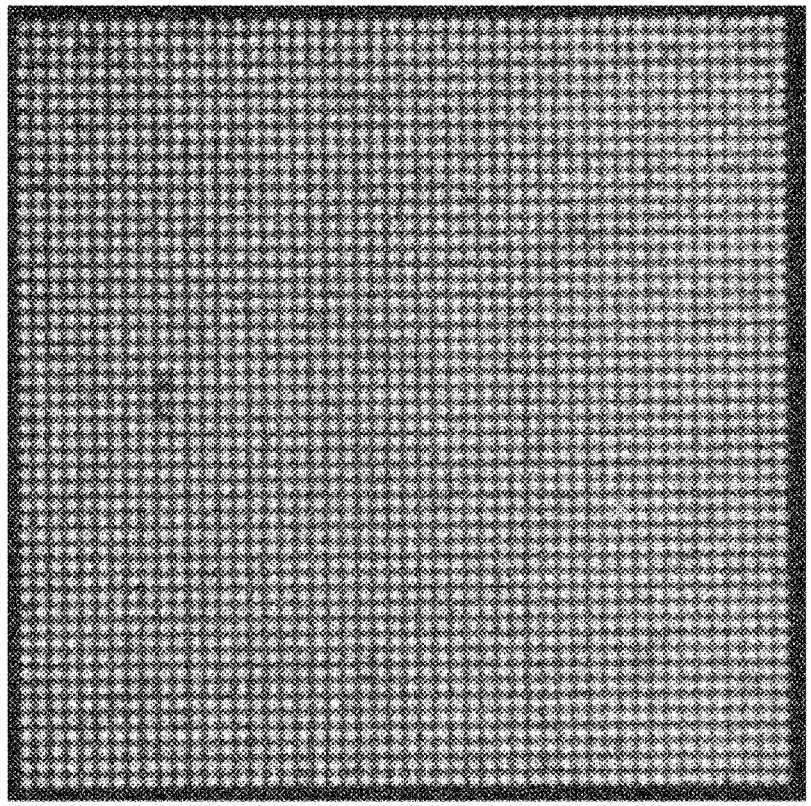
Figure 22:
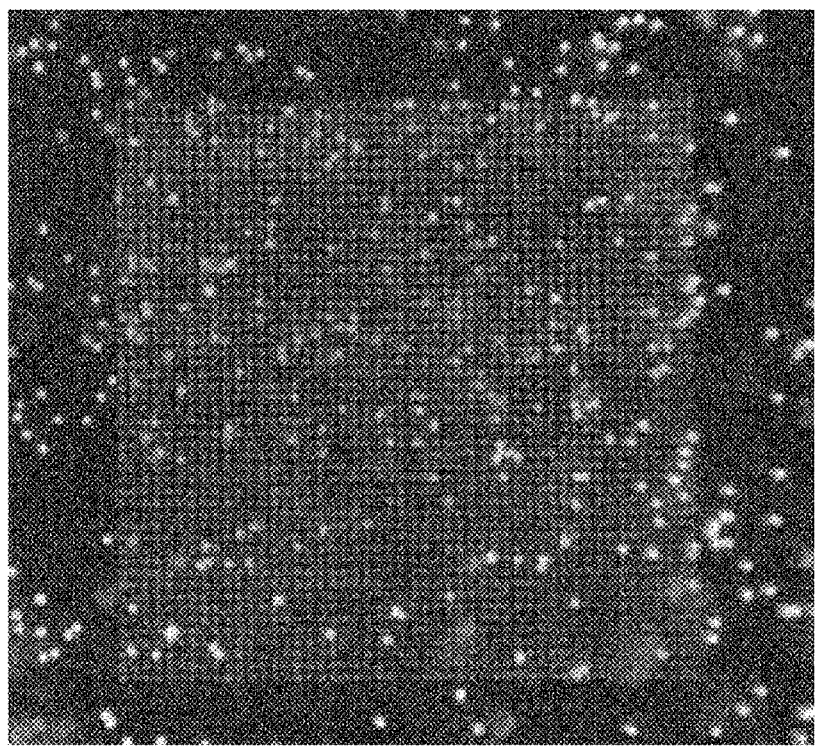
FIG. 22 shows fluorescence images of polystyrene beads' population on device chip with different flow rate and time: (a) bead's population (about 9.6%) with flow rate 10 uL/min for 2 min; (b) bead's population (about 20%) with flow rate 20 uL/min for 2 min; (c) bead's population (about 75.2%) with flow rate 40 uL/min for 1 min; (d) Higher magnification of lined up beads with flow rate 40 uL/min.
Figure 22:
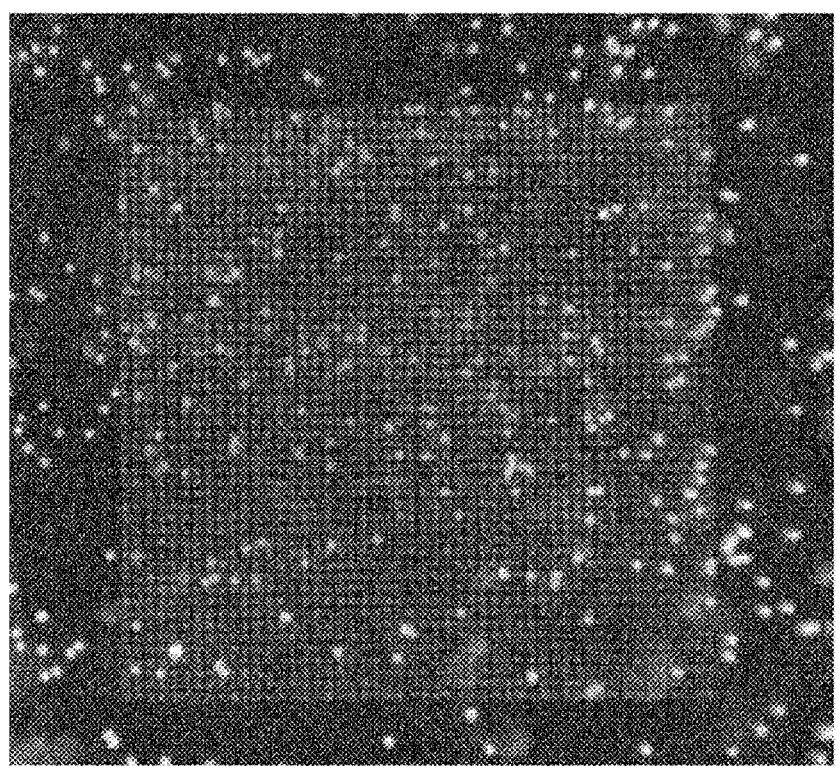
Figure 22:
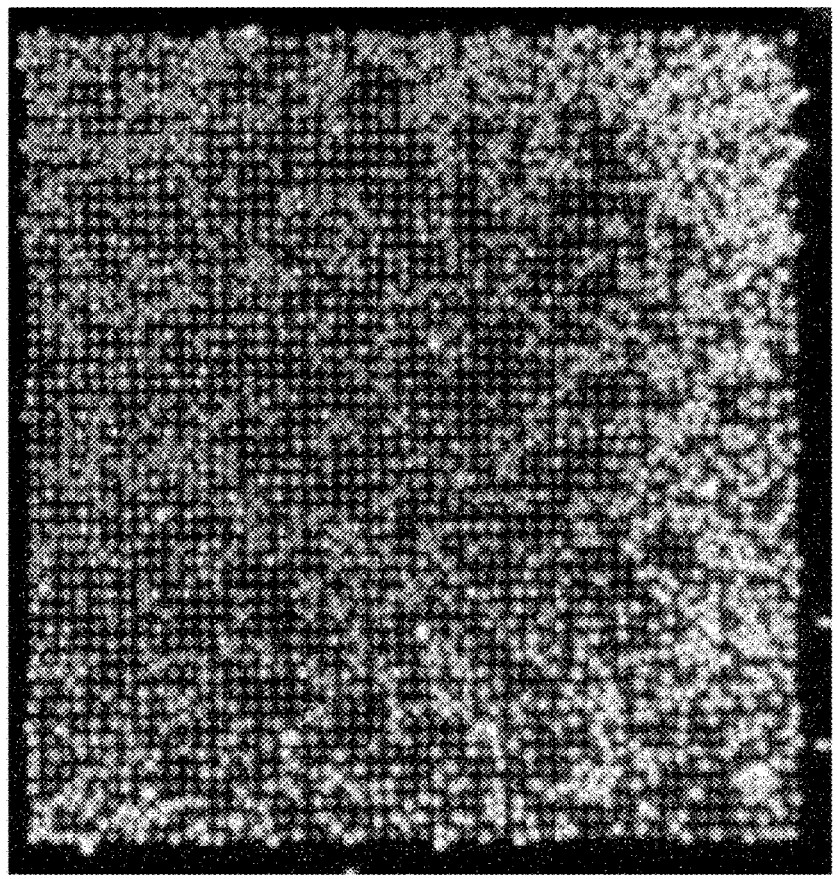
Figure 22:
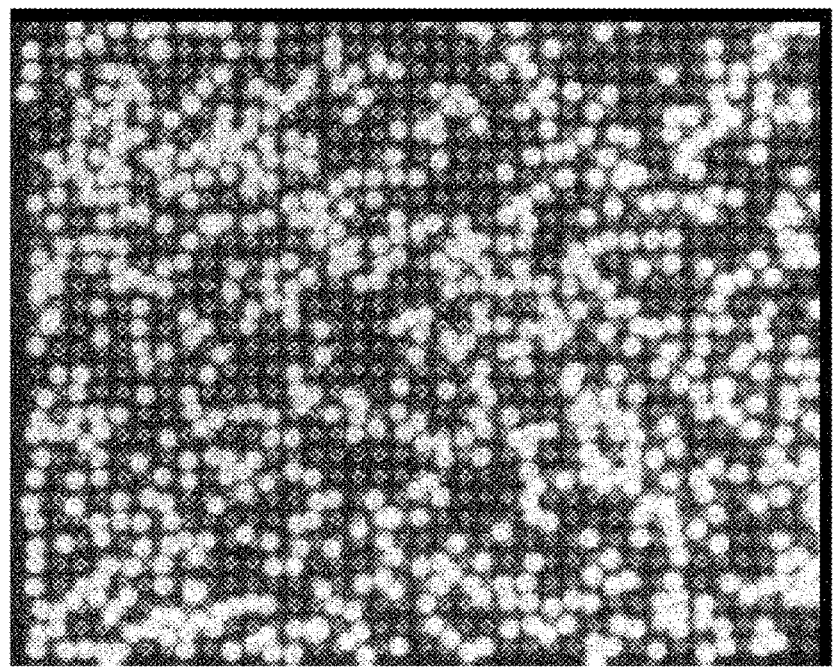
Figure 23:
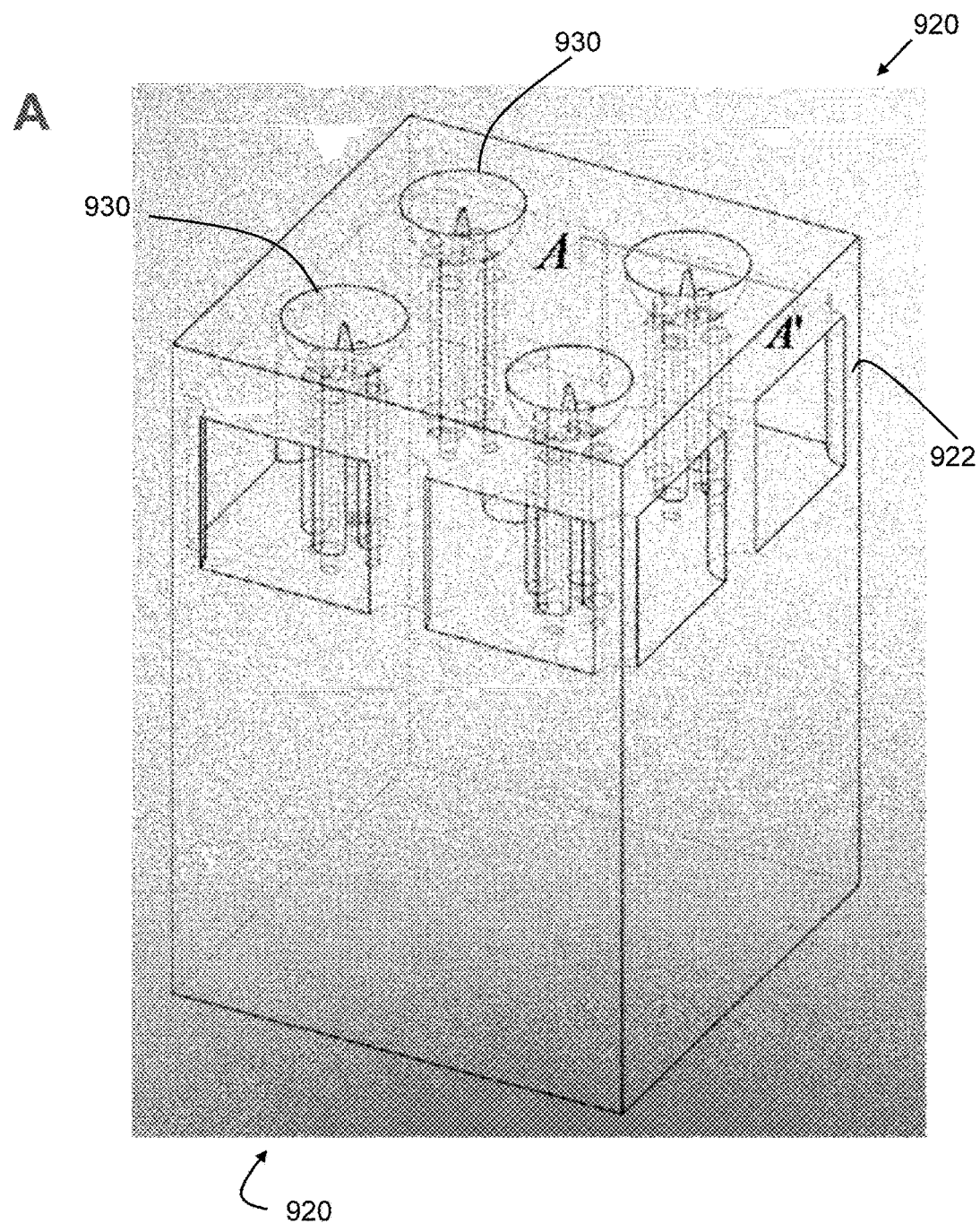
Figure 23:
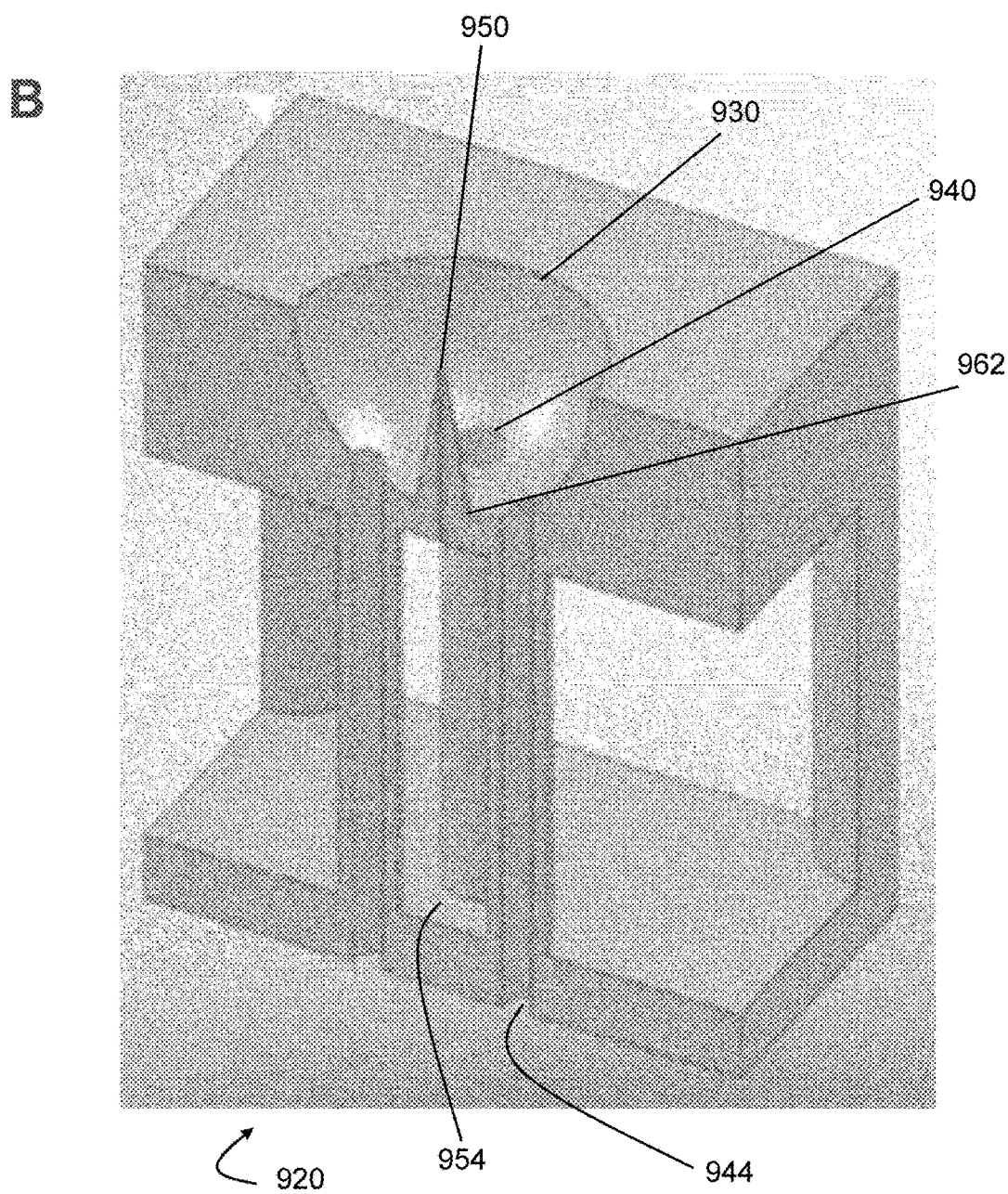
Figure 24:
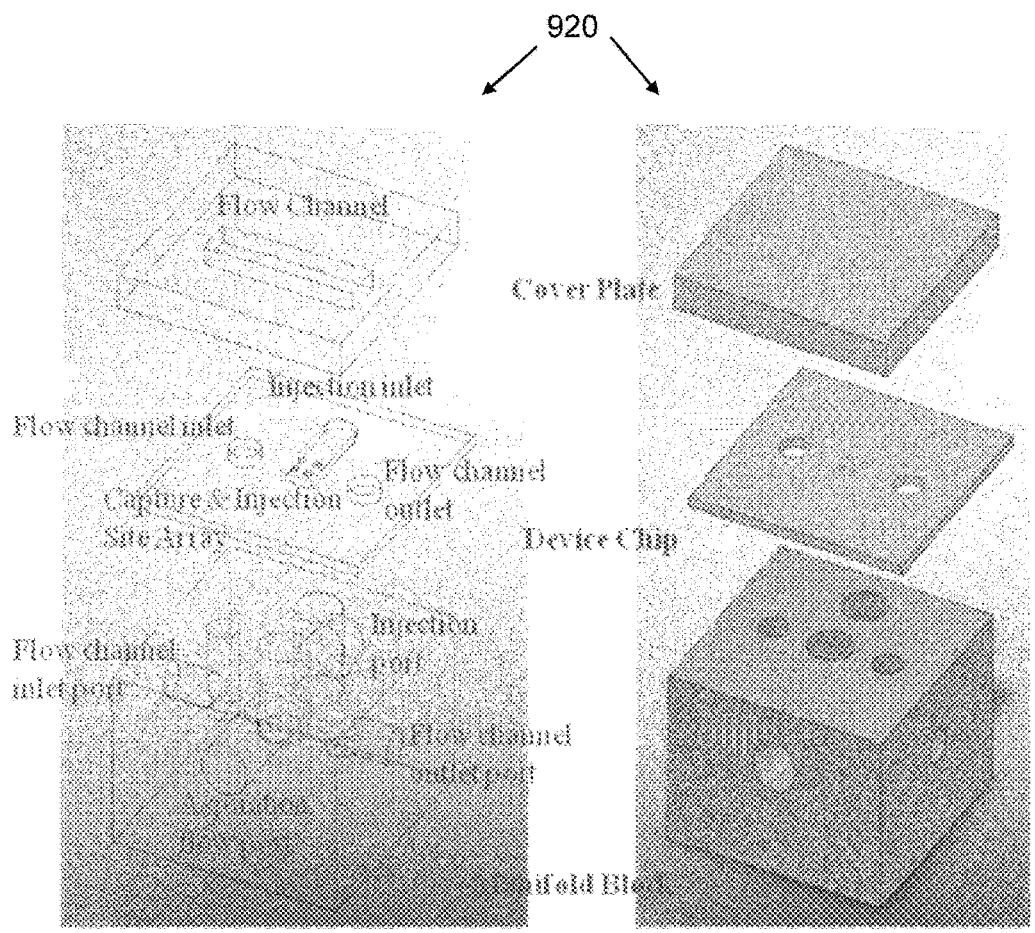
FIG. 24 is a schematic representation of the UHT active microinjection device of FIG. 23 and affiliated parts.
Figure 25:
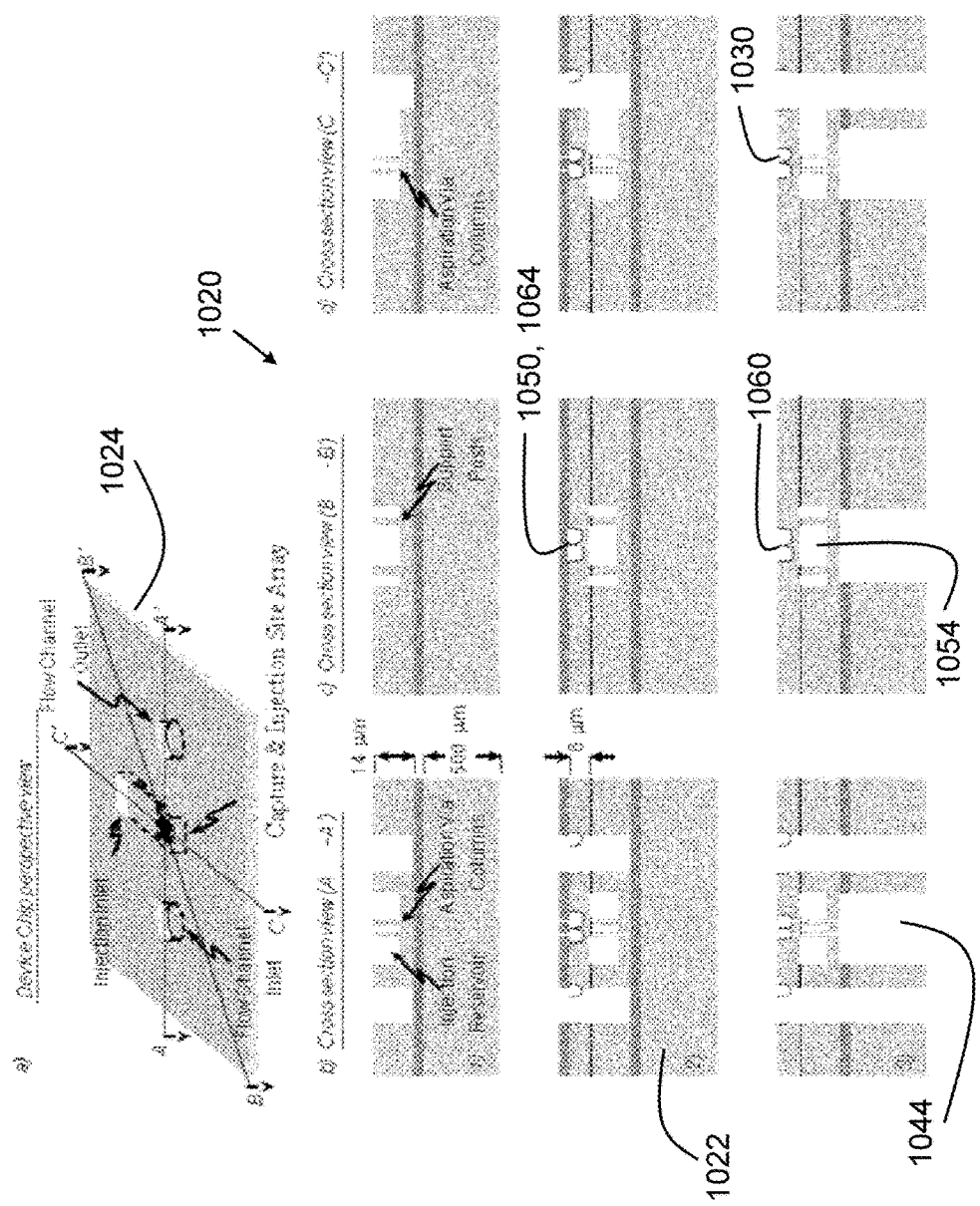
FIG. 25 shows an abridged microfabrication process flow for UHT active microinjection device of FIG. 23. Dotted line indicates the bonded interface. Only one unit cell site is shown for the sake of clarity.

FIG. 13 shows another embodiment of the UHT microinjection device design and assembly. The device is similar to the UHT mechanoporation device described above; however, it further includes an additional independent fluidic circuit for injection functionality.

The Capture Sites retain similar geometry, but include a 0.5 µm diameter lumen within the previously solid Penetrator. The lumen is offset from the Injector apex to produce a solid, sharp tip that minimizes penetration force, membrane deformation, and potential for coring. Injection pressure drop is minimized (0.2 kPa) by the short lumen length and low flow rates required (e.g. ~50 fL/s to inject $1/10^{th}$ of THP-1 cell volume in 1 s). As shown in FIG. 13b, the Aspiration Vias remain connected to the backside port; however, some of the surrounding material is removed to create a reservoir for the Injection circuit. This Reservoir is a continuous volume throughout the array, and its volume per unit cell is ~100 times greater than the injection volume. The multiplicity of Injectors allows control of injection volume, since the collective displacement is ~0.5 nL/s, which is within the capability of a syringe pump equipped with a 0.5 µL syringe ($3 \times 10^5$ to 30 nL/s flow rate capability). Sub-fL balance flow from the Injectors (i.e. continuous efflux) is possible, which may minimize potential for clogging and injection solution dilution, and may also provide an alternative to pulsatile injection (i.e. injection volume would be controlled by residence time on the Injectors). Pressure drop across the Aspiration Vias is similar to the UHT mechanoportation devices, but membrane pressure tolerance is reduced, due to the presence of the Injection Reservoir. Stiffening ribs may be added to the membrane backside to improve pressure tolerance with minimal effect on throughput.

Figure 5:
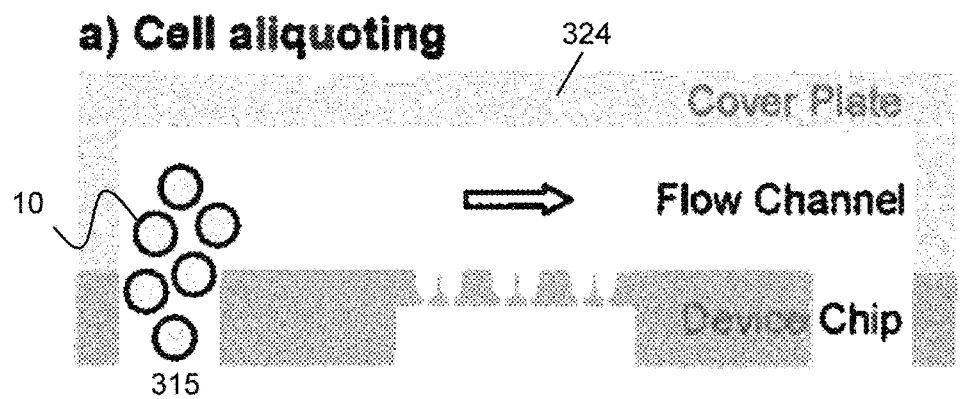
FIG. 5 A is a schematic representation of UHT mechanoporation concept at the package level according to another embodiment. Arrows denote directions of fluid flow in respective fluidic circuits, according to one embodiment of the present invention. B is a block diagram of a method according to one embodiment of the present invention.
Figure 5:
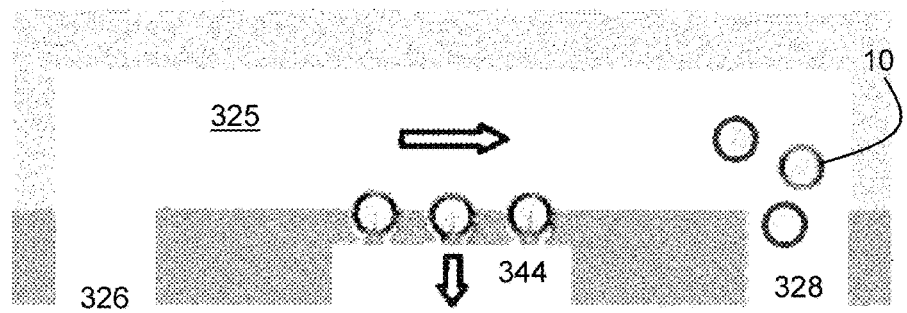
Figure 5:
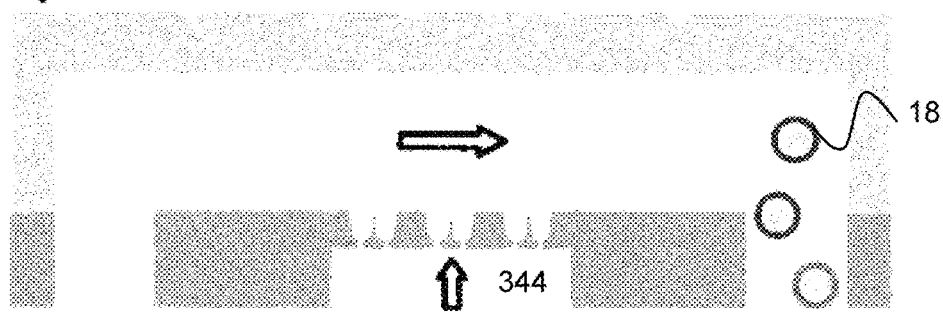
Figure 5:
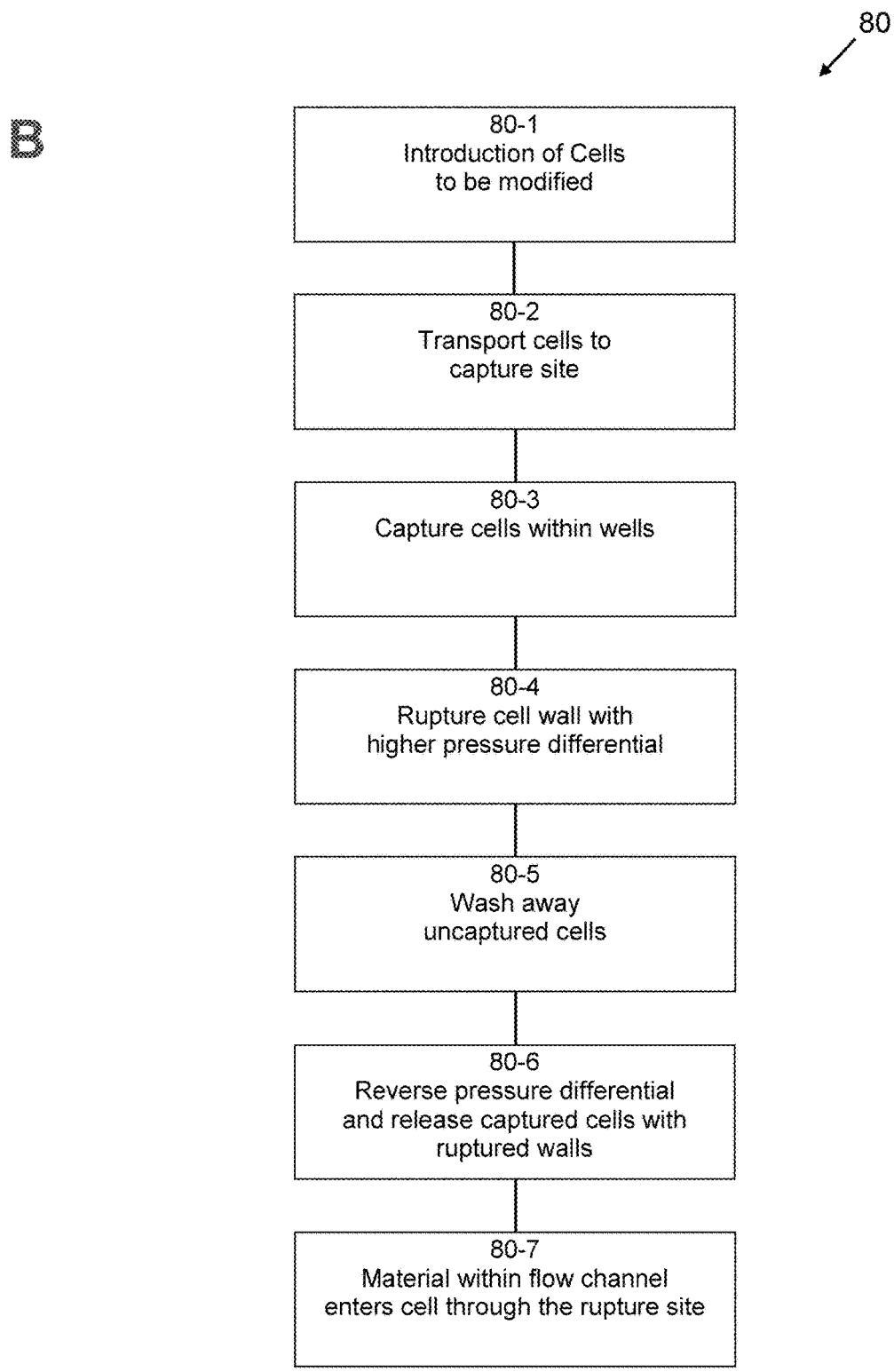

The UHT microinjection device fabrication process builds upon the UHT mechanoporation device fabrication process and includes additional steps to create the Injection Reservoir circuit. Two SOI substrates are used; the first containing the underlying fluidic circuits and backside ports, and the second providing the thin Si layer in which the Capture Sites are defined. As shown in FIG. 5.3, the first substrate 622 contains a 14 µm Si device layer, 2 µm BOX layer, and 500 µm Si handle layer. The frontside is coated with a 0.5 µm $SiO_2$ etch mask using PECVD and lithographically patterned with the Aspiration Via Columns, Support Posts, Injection Inlet, and Flow Channel Inlet/Outlet features. These are transferred to the mask oxide using dry etching. A second lithography step then covers all but the Inlet/Outlet features, which are etched 5 µm using Si DRIE. The photoresist mask is removed and the substrate etched another 10 µm using Si DRIE. The mask oxide is then removed with wet etching and the second SOI substrate is bonded face-to-face (i.e. device layer to device layer). The handle layer of the second SOI substrate is removed using wet etching. The newly exposed BOX layer then serves as an etch mask for the definition of the Capture Sites, which proceed in the same manner as the UHT mechanoporations devices, with the addition of an extra patterning step for the protection of the lumens 664 during the isotropic etch step used to define the Injectors. Finally, the backside ports are etched and the BOX layer is cleared to complete the device. As in the UHT mechanoporation device, thermal oxidation can be performed to produce a thin coating of $SiO_2$ to facilitate subsequent surface functionalization.

Referring to FIG. 13, it can be seen that assembly 620 includes penetrators 660 that each include internal lumens 664 that are in fluid communication with a second source of fluid 654. Each penetrator 660 includes a port 650 proximate to the tip through which material 12 present in supply 654 can flow into the impaled cell 10. Apparatus 620 further includes the various passageways within manifold block 623 to provide fluid and material 12 from source 654. Preferably, source 654 is at a flow rate that is sufficient to inject material 12 into the cell, but insufficient to cause cell 10 to leave its corresponding penetrator 660. However, in some embodiments the cell 10 is released from its capture within well 630 and impalement on penetrator 660 by a combination of increasing flow rate in one or both fluid supply 644 or 654.

Yet other embodiments pertain to increasing functionality through integration of various sensing modalities within the Capture Sites (e.g. impedance, temperature, pH). This provides the opportunity for real-time analyses of expression and its effects at both the single-cell and population levels simultaneously. As such, the inventive concept represents the basis of a broadly enabling and highly versatile technological platform with potential to benefit both biomedical and clinical researchers.

One embodiment pertains to an ultrahigh throughput (UHT) mechanoporation concept. The mechanoporation device is a massively-parallelized MEMS-based platform for passively delivering molecules into living cells via mechanical cell membrane penetration. Disclosed herein are ideas pertaining to device design, fabrication and validation.

Detailed system concept and design is introduced, which integrates functions of cell transfer, capture, penetration and release into a single piece of instrumentation using a microfluidic approach. System operating parameters are analytically analyzed and numerically simulated. The device fabrication in one embodiment utilizes silicon MEMS technologies, and results millimeter-scale device chips containing an array of ten thousand hemispherical capture wells with monolithically integrated solid penetrators. A flow circuit system involving a syringe pump, pressure transducer, and fixture set supporting the device chip was developed. Device validation in one test using K562 cells obtained about 15% average penetration efficiency of live cells after manipulation. The UHT mechanoporation device according to some embodiments provides an efficient and safe method for introducing membrane impermeable molecules into cells with ultrahigh throughput.

The microfabrication and characterization procedure includes five acts, as presented below and shown in FIG. 3.1. A single 100 mm diameter silicon-on-insulator (SOI) substrate with 20 µm Si device layer, 2 µm buried $SiO_2$ (BOX) layer and 500 µm Si handle layer (Ultrasil Corporation) is used.

In act 1, a layer of 1 µm SiO2 mask is deposited on both sides of the SOI substrate using thermal oxidation (CVD Equipment oxidation furnace). The film thickness is verified using Spectroscopic Phase Modulated Ellipsometer (Uvisel FUV 200). Another 2 µm SiO2 mask is deposited on handle layer of the SOI substrate using Plasma Enhanced Chemical Vapor Deposition (PECVD) (Unaxis/Plasma Therm 790).

The following is one process flow outlining the microfabrication procedures of act 1:

(1) Thermal oxidation of both sides of the 4 inch SOI wafer (7 sccm $H_2$, 4 sccm $O_2$, at 1100° C.; 2 hours, average $SiO_2$ film thickness ~1 µm).

(2) PECVD deposit $SiO_2$ film on handle layer of SOI wafer (900 mTorr, 400 sccm 2% $SiH_4$, 900 sccm $N_2O$, and 25 W power; 50 minutes, average film thickness ~2).

In act 2, the elliptical vias are patterned on the device layer of the SOI substrate using projection (stepper) lithography (GCA 6300 i-line system). The aspiration ports connecting the vias on the handle layer of the SOI substrate is patterned using alignment contact lithography (Suss Micro Tec MA6 MA6 contact aligner system). All the patterns are transferred from photoresist to $SiO_2$ mask layer by $CF_4$/$CHF_3$ dry etching (STS Multiplex RIE).

The following is one process flow outlining the microfabrication procedures of act 2:

(1) Projection (stepper) lithography, device layer of SOI wafer—elliptical vias: ((a) Using SPR 955 CM-0.9 positive photoresist; (b) Apply HMDS and spin; (c) Apply resist and spin 3000 rpm for 30 sec; (d) 60 sec pre-exposure bake at 95° C.; (e) Exposure for 1.6 sec; (f) 60 sec post-exposure bake at 110° C.; and (g) Develop in MIF 300 for 70 sec).

(2) $SiO_2$ mask etching-transfer patterns into $SiO_2$ mask from photoresist: ((a) 300 W Power, 100 mTorr pressure, 30 sccm CHF3 and 20 sccm CF4; and (b) ~5 min etch).

(3) Contact lithography, handle layer of SOI wafer-big aspiration port: ((a) Using SPR 220-3.0 positive photoresist; (b) Apply HMDS and spin; (c) Apply resist and spin 2000 rmp for 40 sec; (d) 90 sec pre-exposure bake at 115° C.; (e) Exposure for 20 sec; (f) 90 sec post-exposure bake at 115; and (g) Develop in AZ300MIF for 60 sec).

(4) $SiO_2$ mask etching-transfer patterns into $SiO_2$ mask from photoresist: ((a) 300 W Power, 100 mTorr pressure, 30 sccm CHF3 and 20 sccm CF4; and (b) ~15 min etch).

In act 3, the aspiration port is extended to BOX layer using silicon deep reactive ion etching (DRIE) process (STS MESC ICP Etcher), which is also known as Bosch Process [49, 50]. The process consists of sequential $SF_6$ etching and $C_4F_8$ passivation acts. The Capture Sites monolithically integrated Solid Penetrators are produced by isotropic etching through the elliptical vias on device layer (STS MESC ICP Etcher), which is a process from modified Bosch Process without $C_4F_8$ passivation act. The aspiration vias are then extended to BOX layer by an anisotropic etching (STS MESC ICP Etcher) from modified Bosch process with shorter $SF_6$ etching and $C_4F_8$ passivation acts. Then $SiO_2$ mask layer on device layer is removed by $CF_4$/$CHF_3$ dry etching (STS Multiplex RIE).

In some embodiments, a central projection 60 is created by removing substrate material in a closed pattern. As one example, and as shown herein in FIGS. 3.6, in some embodiments the well 30 is created by removing a pattern of material from multiple locations, but spacing the locations apart and sizing the pattern such that some material remains in the center. Referring to FIG. 3.6a, it can be seen that in one embodiment the pattern is generally elliptical, with the short axes of the ellipses generally intersecting in the center of the closed shape. In FIG. 3.6a, the closed shape is roughly circular, the four elliptical patterns being arranged circumferentially around the circle. The extent of removal in each of the elliptical patterns is sufficient to create an adjoining volume among all of the patterns, but leave a projection of material roughly in the center. In this manner, the resulting projection 60 is integral with the substrate. However, the present invention also contemplates those embodiments in which the projections are subsequently added to a well 30 that was previously created. Further, although what has been shown and described is the placement of four elliptical patterns in a circular manner on the substrate surface, it is understood that the patterns can be of any type, including circular, square, triangular, etc. Further, although an arrangement of four elliptical patterns generally coincident with four elliptical ports (or vias is shown), it is understood that the ports and the removed shapes can be different, and further that they need not be generally aligned and coincident.

The following is one process flow outlining the microfabrication procedures of act 3:

(1) DRIE—aspiration port on handle layer: ((a) Etching act: 700 W ICP coil power, 20 W platen power, 37 mTorr pressure, 130 sccm $SF_6$, 13 sccm $O_2$, 14 sec; (b) Passivation act: 600 W ICP coil power, 0 W platen power, 28 mTorr pressure, 85 sccm $C_4F_8$, 7 sec; and (c) ~2 hour 20 min etch).

(2) Clean samples: Piranha, mixture of $H_2SO_4$ (96% concentration) and $H_2O_2$ (30% concentration), ratio 1:1, ~30 min.

(3) Verification of elliptical vias' feature size and uniformity using SEM (Scanning Electron Microscope) (Leo SUPRA 55 system), as shown in FIG. 3.2.

(4) Silicon isotropic etching-capture wells and Solid Penetrators on device layer: ((a) 500 W ICP coil power, 20 W platen power, 12 mTorr pressure, 95 sccm $SF_6$, 13 sccm $O_2$; and (b) ~4 min 10 sec etch).

(5) Verification of capture wells and Solid Penetrator tops feature size and uniformity using Optical Microscope, as shown in FIG. 3.3.

(6) DRIE—aspiration vias on device layer: ((a) Etching act: 600 W ICP coil power, 17 W platen power, 22 mTorr pressure, 130 sccm $SF_6$, 13 sccm $O_2$, 7 sec; (b) Passivation act: 600 W ICP coil power, 0 W platen power, 16 mTorr pressure, 85 sccm $C_4F_8$, 5 sec; (c) ~11 min etch).

(7) $SiO_2$ mask removal dry etching-device layer: ((a) 300 W Power, 100 mTorr pressure, 30 sccm CHF3 and 20 sccm CF4; and (b) ~4 min 30 sec etch).

(8) Verification of capture wells and Solid Penetrator feature size and uniformity using SEM (Leo SUPRA 55 system), as shown in FIG. 8.

In act 4, $Cl_2$ anisotropic etching (Panasonic ICP Etcher E 620-R&D, UCSB) refines the Solid Penetrator tips to be about 0.5 µm or less, while the bases of the Solid Penetrators are about 2 um in diameter. A following $CF_4$/$O_2$ dry etching (STS Multiplex RIE) takes off $Cl_2$ etching passivation film around Solid Penetrators and on Capture Site side walls.

The following is one process flow outlining the microfabrication procedures of act 4:

(1) Silicon $Cl_2$ anisotropic etching-solid penetrator refinement: (a) 400 W ICP source power, 12 W sample RF power, 1.2 Pa pressure, 10 sccm $Cl_2$; and ~5 min etch).

(2) Verification of capture wells and Solid Penetrator feature size and uniformity using SEM (Leo SUPRA 55 system), as shown in FIG. 3.6.

(3) Chlorine passivation removal dry etching: ((a) 300 W Power, 100 mTorr pressure, 40 sccm 02 and 50 sccm CF4; and Etch time depends on size measurement from (2), e.g. FIG. 3.5 (b) (c)).

(4) Verification of capture wells and Solid Penetrator feature size and uniformity using SEM (Leo SUPRA 55 system), as shown in FIG. 3.7.

In act 5, $SiO_2$ mask layer on handle layer and BOX layer exposed to patterns are removed by $CF_4$/$CHF_3$ dry etching (STS Multiplex RIE), as shown in FIG. 3.8. Piranha cleaning and $O_2$ ashing afterward get rid of organic residuals and particles from the SiO2 mask removal act.

(1) $SiO_2$ mask and BOX layer removal dry etching-handle layer and BOX layer: (a) 300 W power, 100 mTorr, 30 sccm CHF3, 20 sccm CF4; and (b) ~14 min etch).

(2) Clean samples: ((a) Piranha: mixture of $H_2SO_4$ (96% concentration) and $H_2O_2$ (30% concentration), ratio 1:1, 30 min; and (b) $O_2$ ashing: 0.6 mbar, 100 W power, 5 mins).

(3) Verification of aspiration vias and aspiration port feature size and uniformity using SEM (Leo SUPRA 55 system), as shown in FIG. 3.8.

A fixture set was designed and fabricated to support the device chip, as well as provide channels to connect the device chip and external tubing to build the functional flow circuit, as shown in FIG. 4.1. The bottom part of the fixture set is connected with external tubing through the side wall hole, while the tubing is connected with a syringe on syringe pump, providing bi-directional aspiration flow. The top part of the fixture set has a 650 uL reservoir to hold test liquid, which can be sucked onto the device chip underneath directly. The bottom and top parts can clamp the device chip in the middle, and are assembled together by four screws on corners. The fixture set parts are designed and then produced by Computer numerically controlled (CNC) machining (Firstcut, Proto Labs) using polycarbonate.

In the flow circuit, a syringe pump (Harvard Apparatus PHD ULTRA) was used to provide bi-directional constant flow rate flow as aspiration flow, whose syringe is connected with the fixture set using tubing and adaptors (IDEX Health & Science), which are biocompatible and good to use for high-pressure applications. A pressure transducer (Omega DPG 4000-15) was T-off into the main line of the circuit to detect pressure changes.

Test liquid (DI water here) was observed leaking between the device chip and both the bottom/top parts of the fixture set. To seal the gaps, a commercial PDMS film sheet (McMaster-Carr) with 0.125 mm thickness was utilized. After being cut into the device-chip-size pieces, and cut a hole in the middle which is a little bit larger than the Solid Penetrator arrays, the PDMS film pieces are temporarily bonded on both sides of the device chip as gaskets. After operation, temporarily bonded PDMS gaskets can be peeled off and cleaned by Acetone/Isoproponal/DI water rinse. The PDMS gaskets efficiently eliminate leaking.

Utilizing the flow circuit developed, several preliminary functional tests increasing flow rate from 120 uL to 3120 uL for both infuse/withdraw flow were carried out. Corresponding pressure readings for each flow rate were recorded, and compared with analytical calculated results, as shown in FIG. 10.

From the pressure validation test, the device chip membrane robustness was also verified, which is intact after being executed up to about 45 kPa pressure with up to about 3 mm/min flow rate, while the maximum operation flow rate will be about 270 uL with about 1.37 kPa.

In some K562 cell studies, test samples were prepared in a single device operation cycle by: 1) pipetting 50 k cells per 20 uL buffer onto the fixture set reservoir; 2) capturing cells via negative aspiration flow at flow rate 10 uL/min for 30 sec; 3) washing excess uncaptured cells with pipetting; 4) penetrating captured cells using slightly greater negative aspiration flow at flow rate 70 uL/min for 5 sec; 5) releasing penetrated cells using positive aspiration flow at flow rate 1 mL/min for 5 sec; and 6) collecting released cells by pipetting. At least 1 such cycle was performed in each experiment, with up to 3 cycles completed in some experiments. Cell counting utilized manual hematocytometric and automated flow cytometric approaches. Addition of vital dye to the collected cell suspensions enabled quantification of penetration (trypan blue and propidium iodide, for hematocytometric and flow cytometric counting, respectively).

Also prepared were samples for: 1) Background—cells collected, centrifuged, and vortexed; 2) Negative Control—cells pipetted onto device surface, held quiescent for 1 min, collected, and then processed similarly to test samples; and 3) Positive Control—similar to Background samples, but with addition of detergent NP40 to disrupt the cell membrane. Results from hematocytometric counting are shown in Table 1 and indicate cell penetration efficiencies up to 50% greater than other single cycle experiments.

To identify various aspects of the device chip performance, the system was characterized using polystyrene fluorescent beads (15.5 um-mean diameter, P(S/2% DVB)· (480,520), Bangs Laboratories). In the tests, 70 k beads in 20 uL PBS solution were pipetted onto the fixture set reservoir.

It was observed that beads populated unevenly into the capture well arrays. It could be that bubbles were trapped underneath certain capture well arrays and caused this non uniform distribution, as shown in FIG. 4.5 (a). With completely flow circuit flushing before adding beads (or cells in the following tests), bubbles can be minimized.

Since fluorescent beads are rigid solid particles only capturing flow rate and time were varied to improve population efficiency. During beads capturing, negative aspiration flow was stopped before obvious aggregation. Washing excess uncaptured and aggregated beads during capturing helped to get better distribution. Different capturing flow rates were applied, i.e. 10/20/40 uL-min, as shown in FIG. 4.6. Population efficiency is significantly increased from about 9.6% at flow rate 10 uL/min for 2 min, to about 75.2% at flow rate 40 uL/min for 1 min.

MEF cells were prepared in a similar device operation cycle as for the K562 cells. However, the capturing and puncturing of the cells in acts 2 and 4 were stopped when no more significant changes of capturing/puncturing cell population on capture wells were observed. Thus, the capturing act can utilize 110 sec rather than 30 sec for K562 cells, while puncturing act can utilize 40 sec rather than 5 sec for K562 cells. Fluorescent images of MEF cells population on capture wells at different time spots are shown in FIG. 12. Corresponding pressure drop plot from pressure transducer recording is shown in FIG. 12.

FIG. 12 exhibits pressure drop in the MEF cell study as well as in a control study with cell buffers but without cells. In the MEF cell study, the pressure drop achieved the stable value after about 20 sec during cell capturing, which is the same as in the control study. After cell puncturing beginning, the pressure drop kept increasing to a two-fold greater value than the stable value in the control study when the puncturing stopped. The increase within the first 10 sec could result from the pump ramp since it also took about 10 sec for the pressure drop to achieve the stable value in control study. However, as more and more cells being captured and punctured onto the Solid Penetrators, capture wells as well as aspiration vias were gradually populated and filled.

To enable active injection function, Solid Penetrators in some embodiments are replaced with hollow needles, and an injection circuit is introduced into device chip, as shown in FIGS. 5.1a and 5.1b. To enable automated transportation function, flow inlet/outlet ports are added on the device chip, so that affiliated parts can transport cell suspension towards the microneedle arrays as well as collect the manipulated cells. The affiliated parts and active microinjection device chip are shown in FIG. 5.2. The Cover Plate with Flow Channel that directs cells to the capture array and then away for collection can be manufactured with PDMS. The Manifold Block that connects the Aspiration, Flow Channel and Injection ports with external syringe pumps can be fabricated with acrylic.

FIGS. 5.1a and 5.1b depict various views of a device 920 according to another embodiment of the present invention. A generally circular-shaped well 930 is placed in substrate 922. Well 930 defines on its inner hemispherical surface a plurality of ports 940 which are utilized to remove flow from flow channel 925 so as to induce cells 10 toward a capture site, and preferably to be held in place in a well. Well 930 further includes a projection 960 having proximate to its tip a port 950 from which fluid from a second source 954 can be injected into the captured cell.

To fabricate the UHT active microinjection device 920, several acts are used to build the injection circuit 1020, as shown in FIG. 5.3. Two 100 mm—diameter SOI substrates can be used, first of which will provide the thin Si layer in which the Capture Sites is defined, and the second substrate contains the underlying fluidic circuits and backside ports.

The second substrate can be a wafer with 14 urn Si device layer, 2 BOX layer, and 500 um Si handle layer. The device layer of the second substrate can be coated with a 1 um $SiO_2$ etching mask using thermal oxidation and patterned with the Aspiration Via Columns with projection lithography. After transferring those patterns into the $SiO_2$ mask using RIE dry etching, the Injection Inlet and Flow Channel Inlet/Outlet ports can be aligned-patterned with contact-lithography. These are transferred to the $SiO_2$ etching mask using RIE dry etching. Before removing the photoresist mask, the Injection Inlet and Flow channel Inlet/Outlet ports are etched 5 um via Si DRIE. Then the photoresist mask is removed and the device layer is etched another 9 um using Si DRIE till extended to the BOX layer. The $SiO_2$ mask is then removed with RIE dry etching. The aspiration/Flow Channel Inlet/Outlet ports on substrate handle layer are etched by DIRE Bosch process as in current device and extended to BOX layer. The BOX layer exposed to ports cam be dry etched using RIE.

The handle layer of the first substrate can be removed using wet etching in advance. The exposed BOX layer then serves as an etching mask for the definition of the Capture Sites and Injection needles. The aspiration vias and injection lumens are projection lithographically patterned and transferred into the BOX layer using RIE dry etching. The Injection and Flow Channel Inlet/Outlet ports can be patterned using contact-lithography and transferred into the BOX layer with RIE dry etching. After isotropic etching to define the Capture Sites and Solid Penetrators, Si DRIE can be etched through the Injection and Flow Channel Inlet/Outlet ports, as well as the aspiration vias and injection lumens. The BOX layer can be etched with RIE dry etching. The second substrate can be bonded face to face with the first substrate.

Various aspects of different embodiments of the present invention are expressed in paragraphs X1, X2, X3, X4 and X5 as follows:

X1. One aspect of the present invention pertains to an apparatus for manipulation of biological cells. The apparatus preferably includes a substrate having surface and a plurality of wells, each well having a shape at the surface adapted and configured to support a portion of a corresponding one of the cells, each said well including a port in fluid communication with a port of each said other well, so as to simultaneously apply a pressure to the portions and to simultaneously capture and hold the plurality of cells.

X2. One aspect of the present invention pertains to an apparatus for manipulation of biological cells. The apparatus preferably includes a substrate having a surface and a plurality of wells, each well having a shape at the surface adapted and configured to support a portion of a corresponding one of the cells, each said well including a port in fluid communication with a port of each said other well, so as to simultaneously flow fluid from the first source into or out of the plurality of wells, and to capture or hold, respectively, the plurality of cells in their corresponding wells.

X3. Another aspect of the present invention pertains to an apparatus for manipulation of biological cells. The apparatus preferably includes a first source of fluid, and a second source of fluid. The apparatus preferably includes a substrate having surface and a plurality of wells, each said well having an interior adapted and configured to hold therein at least a portion of one of the cells, each said well including a first port in fluid communication with said first source, each said well including a second port in fluid communication with said second source.

X4. Another aspect of the present invention pertains to a method for manipulating a biological cell. The method preferably includes providing a substrate having a surface and a depression in that surface. The method preferably includes introducing the cell to the surface. The method preferably includes capturing the cell within the depression. The method preferably includes capturing cells by hydrodynamic drag produced by fluid flow through defined areas within the substrate, followed possibly by rupturing the wall of the cell by said applying at a higher rate.

X5. Another aspect of the present invention pertains to an apparatus for manipulation of biological cells. The apparatus preferably includes a substrate having a surface and a plurality of fluid ports, each said fluid port being in fluid communication with each other port by way of one or more fluid passageways within the substrate. Each port has a shape adapted and configured to support thereon a corresponding cell. The substrate further includes a projection having a tip that is adapted and configured to be in contact with the corresponding cell captured by the corresponding port preferably from within the substrate.

Yet other embodiments pertain to any of the previous statements X1, X2, X3, X4, or X5, which are combined with one or more of the following other aspects Wherein each said well has a bottom, and each said projection extends from a bottom of the corresponding well to a location proximate to the surface of the substrate.

Wherein said projection includes a base and a tip, the base being integrated into the substrate.

Wherein said projection having a length between a base and a tip, said projection having a cross-sectional area that increases along the length in a direction from the tip to the base.

Wherein said projection is adapted and configured to penetrate the wall of a cell.

Wherein each said projection includes a lumen, and/or wherein each said lumen is in fluid communication with each other said lumen.

Wherein said first source includes means for controlling the flow of the first fluid into or out of the first port, and said second source includes means for controlling the flow of the second fluid into or out of the second port.

Wherein said projection includes a sharp tip, or a blunted tip.

Wherein the boundary shape at the surface is adapted and configured to support one and only one cell.

Wherein the length of the boundary shape is less than the circumference of a cell.

Wherein the boundary shape is generally circular, and the diameter of the boundary is less than about fifty microns, or wherein the boundary is less than about twenty microns.

Wherein said plurality of wells are equally spaced apart in each of two orthogonal directions.

Wherein the surface of said substrate is exposed to an ambient pressure, and the first pressure is less than the ambient pressure.

Wherein said second source of fluid includes material to be introduced into the interior of each said well, and/or wherein said second source of fluid includes material to be injected into the interior of the cells.

Wherein each said well includes a plurality of first ports, and/or wherein each second port is located centrally to the corresponding plurality of said first ports.

Wherein each said second port has a shape that projects into the interior of the corresponding well.

Wherein each said well includes one and only one second port.

Wherein each said first port has a greatest dimension that is less than about three microns.

Wherein each said first port projects a shape that is generally non-circular and/or elliptical.

Wherein the substrate includes a first flow channel for introducing cells to the surface of the substrate and a second flow channel for removing cells from surface of the substrate.

Which further comprises a cover, said cover and said substrate defining an enclosed volume in which cells are exposed to said wells.

Wherein a portion of the captured cell is within the depression and another portion is outside the depression, and said applying is to the one portion relative to the other portion.

Wherein the depression includes a projection that contacts the wall of the capture cell, and said rupturing is by concentrating stress on the cell wall by the depression.

Wherein depression has a bottom and the projection projects from the bottom.

Which further comprises injecting material into the ruptured wall of the captured cell.

Which further comprises washing away any uncaptured cells before said applying.

Which further comprises releasing the captured cell with the ruptured wall into a solution including a biologically active material.

Wherein the pressure differential is a positive pressure differential, and which further comprises releasing the captured cell with the ruptured wall by applying a negative pressure differential.

While the inventions have been illustrated and described in detail in the drawings and foregoing description, the same is to be considered as illustrative and not restrictive in character, it being understood that only certain embodiments have been shown and described and that all changes and modifications that come within the spirit of the invention are desired to be protected.

The invention claimed is:

1. An apparatus for manipulation of biological cells, comprising:
   a substrate having a surface and a plurality of wells,
   each said well having a boundary shape at the surface adapted and configured to support thereon a cell,
   each said well having a bottom and including a projection extending from the bottom toward the surface of the substrate, wherein said projection is adapted and configured to penetrate a cell membrane and/or wall of the cell,
   a single common fluid flow channel that is fluidly in direct contact with each of the plurality of wells, wherein the fluid flow channel is capable of exposing each of the plurality of wells to biological cells in a simultaneous manner, and wherein the fluid flow channel can be fluidly connected to a first source of fluid, and
   a plurality of aspiration vias that have unobstructed access to each of the wells and to a cell bound at the boundary shape of the wells, wherein the plurality of aspiration vias are fluidly connected to a second source of fluid, to which negative pressure can be applied to provide suction that captures the cell, or to which positive pressure can be applied to release the cell, wherein the plurality of aspiration vias are fluidly in contact with other wells in said plurality of wells, wherein a pressure in each of the aspiration vias is capable of being directly applied to a cell membrane of a cell captured at the boundary shape, wherein the pressure in each of the aspiration vias is capable of being varied in relation to the pressure in the common fluid flow channel, wherein the plurality of aspiration vias is configured to provide uniform tension on the cell membrane of a cell captured at the boundary shape, wherein the plurality of aspiration vias are located in the bottom of each of said wells and wherein at least two of the plurality of aspiration vias are located opposite one another and separated by the projection and whose axis are substantially perpendicular to the surface.

2. The apparatus of claim 1, wherein each said well has a bottom, and each said projection extends from a bottom of the corresponding well to a location proximate to the surface of the substrate.

3. The apparatus of claim 1, wherein said projection includes a base and a tip, the base being integrated into the substrate.

4. The apparatus of claim 1, wherein said projection having a length between a base and a tip, said projection having a cross-sectional area that increases along the length in a direction from the tip to the base.

5. The apparatus of claim 1, wherein each said projection includes a lumen, and wherein the lumen can be fluidly connected to a third source of fluid.

6. The apparatus of claim 5, wherein each said lumen is in fluid communication with each other said lumen.

7. The apparatus of claim 1, wherein said projection includes a sharp tip.

8. The apparatus of claim 1, wherein the boundary shape at the surface is adapted and configured to support only one cell.

9. The apparatus of claim 1, wherein the circumference of the boundary shape is less than the circumference of a cell.

10. The apparatus of claim 1, wherein the boundary shape is generally circular and the diameter of the boundary is less than about fifty microns.

11. The apparatus of claim 1, wherein said plurality of wells are equally spaced apart in each of two orthogonal directions.

12. The apparatus of claim 5, wherein the longitudinal axis of the plurality of aspiration vias is parallel to the lumen.

13. An apparatus for manipulation of biological cells, comprising:

a substrate having a surface, one or more inlet ports and one or more outlet ports that extend entirely through the thickness of the substrate, and a plurality of wells, wherein each of the plurality of wells has an interior adapted and configured to hold therein at least a portion of a cell, wherein each of the plurality of wells comprises a plurality of aspiration vias that have unobstructed access to each of the wells and to a cell bound at a boundary shape of the wells, wherein the plurality of aspiration vias are fluidly in contact with other wells in said plurality of wells, wherein a pressure in each of the aspiration vias is capable of being directly applied to a cell membrane of a cell captured at the boundary shape, wherein the pressure in each of the aspiration vias is capable of being varied in relation to the pressure in the common fluid flow channel, wherein the plurality of aspiration vias is configured to provide uniform tension on the cell membrane of a cell captured at the boundary shape, wherein the plurality of aspiration vias are located in the bottom of each of said wells and wherein at least two of the plurality of aspiration vias are located opposite one another and separated by the projection and whose axis are substantially perpendicular to the surface, and a projection extending from a bottom of each of the wells toward the surface of the substrate, wherein said projection is adapted and configured to penetrate a cell membrane and/or wall of the cell, a cover plate comprising a fluid flow channel, wherein the fluid flow channel can be fluidly connected with the one or more inlet ports, the one or more outlet ports and the plurality of wells of the substrate;

a fluid inlet flow channel that can be fluidly connected with the one or more inlet ports and which can be fluidly connected with a first source of fluid; and a fluid outlet flow channel that is in fluid communication with the one or more outlet ports.

14. The apparatus of claim 13, wherein the one or more aspiration vias have a greatest dimension that is less than about three microns.

15. The apparatus of claim 13, wherein the one or more aspiration vias are generally elliptical in shape.

16. The apparatus of claim 13, wherein the substrate further comprises an injection inlet that can be fluidly connected to an injection reservoir, and wherein the injection reservoir can be fluidly connected to a third source of fluid.

17. The apparatus of claim 16, wherein each said projection includes a lumen, and wherein the lumen is fluidly connected to the injection inlet through the injection reservoir.

18. A method for manipulating a biological cell, comprising:
provinding a substrate of claim 1;
introducing the cell to the surface;
capturing the cell within a well of the plurality of wells by applying a first hydrodynamic force; and
applying a second hydrodynamic force on the captured cell and locally rupturing the membrane and/or wall of the cell with the projection.

19. The method of claim 18, wherein the first hydrodynamic force is applied with sufficient force to capture the cell within a well of the plurality of wells but is not of sufficient force to rupture the membrane and/or wall of the cell with the projection; and wherein the second hydrodynamic force is applied in a quick and limited temporal manner so as to drive the membrane and/or wall of the captured cell onto the projection, and wherein once the captured cell is punctured the second hydrodynamic force may be reversed to release the captured cell or reduced to hold the cell on the projection.

20. The method of claim 18, which further comprises injecting material into the captured cell.

21. The method of claim 18, which further comprises washing away any uncaptured cells prior to applying the second hydrodynamic force.

22. The method of claim 18, which further comprises releasing the captured cell with the locally ruptured wall into a solution including a biologically active material.

23. The method of claim 18, wherein cell capture is effected by fluid being aspirated through the aspiration vias, and cell release is effected by fluid flow through the plurality of the aspiration vias into said corresponding wells.

24. The method of claim 21, which further comprises reintroducing the washed out cells to the surface.

* * * * *

UNITED STATES PATENT AND TRADEMARK OFFICE
CERTIFICATE OF CORRECTION

PATENT NO. : 9,885,059 B2  
APPLICATION NO. : 14/379486  
DATED : February 6, 2018  
INVENTOR(S) : Christopher Ballas et al.

Page 1 of 1

It is certified that error appears in the above-identified patent and that said Letters Patent is hereby corrected as shown below:

In the Specification

In Column 3 at Line 28, change "5 A" to --5. (A)--.

In Column 3 at Line 32, change "B" to --(B)--.

In Column 4 at Line 15, change "FIG." to --FIGS.--.

In Column 5 at Line 8, change "23 a)" to --23. (a)--.

In Column 5 at Line 10, change "b" to --(b)--.

In Column 5 at Line 12, change "a." to --(a).--.

In Column 13 at Line 35, change "mechanoportation" to --mechanoporation--.

In Column 17 at Line 39, change "lsoproponal" to --Isopropanol--.

In Column 20 at Line 43, after "aspects" insert --.--.

Signed and Sealed this  
Eighteenth Day of June, 2019

Andrei Iancu  
*Director of the United States Patent and Trademark Office*